(12) United States Patent
McGrath

(10) Patent No.: US 8,008,353 B2
(45) Date of Patent: Aug. 30, 2011

(54) METHODS FOR MODULATING MACROPHAGE PROLIFERATION USING POLYAMINE ANALOGS

(75) Inventor: Michael S. McGrath, Burlingame, CA (US)

(73) Assignee: The Regents of the University of California, Oakland, CA (US)

( * ) Notice: Subject to any disclaimer, the term of this patent is extended or adjusted under 35 U.S.C. 154(b) by 1233 days.

(21) Appl. No.: 11/022,153

(22) Filed: Dec. 22, 2004

(65) Prior Publication Data

US 2005/0159493 A1   Jul. 21, 2005

Related U.S. Application Data

(63) Continuation of application No. 09/179,383, filed on Oct. 26, 1998, now Pat. No. 7,087,648.

(60) Provisional application No. 60/063,317, filed on Oct. 27, 1997, provisional application No. 60/063,318, filed on Oct. 27, 1997.

(51) Int. Cl.
   A61K 31/155 (2006.01)
(52) U.S. Cl. .................................. 514/635; 514/634
(58) Field of Classification Search .............. 514/634, 514/635
See application file for complete search history.

(56) References Cited

U.S. PATENT DOCUMENTS

| | | | |
|---|---|---|---|
| 4,201,788 A | 5/1980 | Voorhees et al. |
| 4,847,257 A | 7/1989 | Hupe et al. |
| 5,037,846 A | 8/1991 | Saccomano et al. |
| 5,091,576 A | 2/1992 | Bergeron |
| 5,242,947 A | 9/1993 | Cherksey et al. |
| 5,460,807 A | 10/1995 | Cardin et al. |
| 5,498,522 A | 3/1996 | Porter et al. |
| 5,516,807 A | 5/1996 | Hupe et al. |
| 5,541,230 A | 7/1996 | Basu et al. |
| 5,580,715 A | 12/1996 | McGrath et al. |
| 5,639,600 A | 6/1997 | McGrath et al. |
| 5,665,588 A | 9/1997 | Kornbluth |
| 5,672,746 A | 9/1997 | Nau et al. |
| 5,677,350 A | 10/1997 | Frydman |
| 5,679,682 A | 10/1997 | Bergeron |
| 5,880,161 A | 3/1999 | Basu et al. |

(Continued)

FOREIGN PATENT DOCUMENTS

EP   0 162 413   11/1985

(Continued)

OTHER PUBLICATIONS

Rizzo et al. "Pharmacokinetic profile of mitoguazone (MGBG) in patient with AIDS related non-Hodgkin's lymphoma," Investigational New Drugs, 1996, vol. 14, pp. 227-234.*

(Continued)

Primary Examiner — Shengjun Wang
(74) Attorney, Agent, or Firm — Carol L. Francis; Bozicevic, Field & Francis LLP

(57) ABSTRACT

Methods for modulating macrophage proliferation in an individual afflicted with or at risk for a macrophage-associated disease are provided. The methods employ a polyamine analog, or salt or protected derivative thereof. Macrophage proliferation has been implicated in a number of serious disorders, including AIDS (HIV)-associated dementia, AIDS-associated non-Hodgkin's lymphoma, and Alzheimer's disease. The invention also provides methods for aiding diagnosis and monitoring therapy of a macrophage-associated non-HIV associated dementia, especially Alzheimer's disease. The invention also provides methods of delaying development of macrophage-associated non-HIV associated dementias, including Alzheimer's disease, which entail administration of an agent which modulates macrophage proliferation.

8 Claims, 8 Drawing Sheets

U.S. PATENT DOCUMENTS

| | | | |
|---|---|---|---|
| 5,886,051 | A | 3/1999 | Bergeron, Jr. et al. |
| 5,889,061 | A | 3/1999 | Frydman et al. |
| 6,392,098 | B1 | 5/2002 | Frydman et al. |

FOREIGN PATENT DOCUMENTS

| | | |
|---|---|---|
| EP | 0 277 635 | 8/1988 |
| EP | 0 399 519 | 11/1990 |
| EP | 0 415 801 | 3/1991 |
| EP | 0 415 801 A1 | 3/1991 |
| EP | 0 436 332 | 7/1991 |
| JP | 60-6348 | 2/1985 |
| JP | 08217670 | 8/1996 |
| WO | WO 92 13548 | 8/1992 |
| WO | WO 93 04036 | 3/1993 |
| WO | WO 93 14782 | 8/1993 |
| WO | WO 96 04019 | 2/1996 |
| WO | WO 97/33175 | 12/1997 |
| WO | WO 98 17624 | 4/1998 |
| WO | WO 99 03823 | 1/1999 |

OTHER PUBLICATIONS

Von Hoff "MGBG: Teaching an old drug new tricks," Annals of Oncology, 1994, vol. 5, pp. 487-493.*

Basu et al. "The Ability of Polyamine Analogues to Induce Z-DNA Structure in Synthetic Ploynucleotides in Vitro in Inversely Correlates with their Effects on Cytotoxcity of Cisdiaminedichloroplatinum (II) (CDDP) in Human Brain Tumor Cell Lines" (1996) Anticancer Res. 16:39-48.

Bellevue, III et al. "Structural Comparison of Alkylpolyamine Analogues with Potent in Vitro Antitumor or Antiparasitic Activity" (1996) Bioorg. Med. Chem. Lett. 6:2765-2770.

Bergeron et al. "Two Polyamine Analogs (BE-4-4-4 and BE-4-4-4-4) Directly Affect Growth, Survival, and Cell Cycle Progression in Two Human Brain Tumor Cell Lines" (1995) Cancer Chemother. Pharmacol. 36:411-417.

Bersnstein et al. "The Cellular Localization of the L-Orinthine Decarboxylase Polyamine System in Normal and Diseased Central Nervous Systems," Progress in Neurobiology 57(5):485-505, 1999.

Bitonti et al. "Bis(benzyl)poluamine Analogs Inhibit the Growth of Chloroquine-Resistant Human Malaria Parasites (*Plasmodium falciparum*) In Vitro and In Combination With α-Difluoromethylomithine Cure Murine Malaria" (1989) Proc. Natl. Acad. Sci. USA 86:651-655.

Chiang et al. "Antihuman Immunodeficiency Virus (HIV-1) Activities of Inhibitors of Polyamine Pathways," J. Biomed. Sci. 3(2):78-81, 1996.

Fields et al., "Fields Virology," vol. 2, 1996, Lippincott Williams & Wilkins, pp. 2418-2419.

Fogel-Petrovic et al. "Effects of Polyamines, Polyamine Analogs, and Inhibitors of Protein Synthesis on Spermidine-Spermine N'-Acetyltransferase Gene Expression," (1996) Biochemistry 35:14436-14444.

Gabrielian et al., "Effect of Leukopenia on Experimental Post-Traumatic Retinal Detachment" (1993) Curr. Eye Res. 13:1-9.

Greene et al., Protective Groups in Organic Synthesis, $2^{nd}$ Ed., John Wiley & Sons, Inc. New York. (Table of Contents) (1991).

Hibasami et al., "Antitumor Effect of a New Multienzyme Inhibitor of Polyamine Synthetic Pathway, Methyglyocal-Bis(Cyclopentylamidinohydrazone), Against Human and Mouse Leukemia Cells" (1989) Cancer Res. 49:2065-2068.

Kackzmarek et al., "Inhibitors of Polyamine Biosynthesis Block Tumor Necrosis Factor-Induced Activation of Macrophages," Cancer Res. 52(7):1891-1894, 1992.

Kramer et al., "Use of 4-Fluoro-l-ornithine to Monitor Metabolic Flex Through The Polyamine Biosynthetic Pathway" (1995) Biochem. Pharmacol. 50:1433-1443.

Lim et al., "MGBG Therapy of Relasped Extralymphatic HIV-Associated Non-Hodgkins Lymphoma (HIV NHL)," (Mar. 14, 1995) Proc. Annu. Meet. Am. Soc. Clin. Oncol. 14:A1274.

Marton et al., "Polyamines As Targets for Therapeutic Intervention" (1995) Ann Rev. Pharmacol. Toxicol. 35:55-91.

Mascolini. "Oncologists Scout New Direction for KS and Lymphoma Therapies," (1995) J. Int. Assoc. Physicians Aids Care 1(5):10-14.

McGrath et al., "Indentification of A Clonal Form Of HIV In Early Kaposi's Sarcoma: Evidence For A Novel Model Of Oncogenesis, 'Sequential Neoplasia'"(1995) J. Acquired Inn. Def. Syn. Hum. Retro. 8:379-385.

Messina et al., "Polyamine Involvement In Functional Activation of Human Macrophages," (1992) J. Leukoc. Biol. 52(6):585-587.

Miles et al., "Curative Therapy of AIDS Cancers," (Jul. 1, 1996) Int. Conf. AIDS. XI(1):28.

Mukhopadhyay et al., "Effects of Bis(Benzl)Polyamine Analogs On Leishmania Donavani Promatigotes," (1995)Exper. Parasitology 81:39-46.

Pennings et al., "Sensitization of TNF-Induced Apoptosis With Polyamine Synthesis Inhibitors in Difference Human and Murine Tumor Cell Lines,"Cytokine 10(6):423-431, 1998.

Porter et al., "Polyamine Inhibitors and Analogues As Potential Anticancer Agents," (1992) Falk Symposium 62-Polyamines In The Gastrointestinal Tract Chapter 31, pp. 301-322, 1992.

Prakash et al., "Antitumor Activity of Norspemidine, A Structural Homologue of the Natural Polyamine Spermindine," Anticancer Research 8:563-568 (1998).

Pulliam et al., "Unique Monocyte Subset in Patients with AIDS Dementia," (1997) Lancet 349:692-695.

Reminton's Pharmaceutical Sciences, $18^{th}$ Edition, Mack Publishing (1990) (Table of Contents).

Rizzo et al., "Pharmacokinetic Profile of Mitoguazone (MGBG) In Patients With AIDS Related Non-Hodgkins Llymphoma," (1996), Inventigational New Drug, vol. 14, pp. 227-234.

Shiramizu et al., "Identification of a Common Clonal Human Immunodeficiency Virus Integration Site in Human Immunodeficiency Virus-Associated Lymphomas", (1994) Cancer Res. 54:2069-2072.

Von Hoff, "MGBG: Teaching an Old Drug New Tricks," (1994), Annals of Oncology, vol. 5. pages 487-493.

Wojewodzka et al., "Structure-Activity Relationship of Polyamine Derivatives of 1, 3-Dichloracetone-Thiosemicarbazone: Induction of Metastases and Increase In Sialylation of Murine Lymphoma L5178Y-R Cells," Chem. Biol. Interactions, 74 (1990) 221-223.

* cited by examiner

*60% of input CD14 cells were PCNA+;assay after 96hr drug exposure and culture

METHODS FOR MODULATING MACROPHAGE PROLIFERATION USING POLYAMINE ANALOGS

CROSS-REFERENCE TO RELATED APPLICATIONS

This application is a continuation of U.S. application Ser. No. 09/179,383, filed Oct. 26, 1998, which application claims the benefit of U.S. Provisional Application Ser. Nos. 60/063,317 and 60/063,318, both filed Oct. 27, 1997, each of which applications are incorporated by reference.

STATEMENT OF RIGHTS TO INVENTIONS MADE UNDER FEDERALLY SPONSORED RESEARCH

This invention was made in part during work supported by a grant from one or more government agencies. The government has certain rights in the invention.

TECHNICAL FIELD

This invention relates to macrophage proliferation. More specifically, it relates to the use of polyamine analogs or salts or protected derivatives thereof to modulate macrophage proliferation, particularly in individuals afflicted with or at risk for a macrophage-associated disease. The invention also relates to methods of aiding diagnosis monitoring therapy, and delaying development of macrophage proliferation disorders (in the context of non-HIV associated dementias, such as Alzheimer's disease) that entail detection and/or modulation of macrophage proliferation.

BACKGROUND ART

Cell proliferative diseases represent a major health problem and threat worldwide. Such diseases are characterized by the single or multiple abnormal proliferation of cells, groups of cells or tissue(s). See U.S. Pat. No. 5,665,588. Cell proliferative diseases include, but are not limited to, AIDS dementia, various cancers, atherosclerosis, vitreoretinopathy, psoriasis, neurodegenerative disorders and nephropathy. See U.S. Pat. Nos. 5,639,600, 4,847,257 and 5,672,746. Dementias, or progressive mental failures, particularly present a serious worldwide health problem, both in terms of the extent of debilitation and health care costs. Dementias include non-HIV-associated dementias (such as Alzheimer's disease or AD) and HIV-associated dementia.

Macrophages are terminally differentiated cells generally incapable of further cell division. Surprisingly, macrophage proliferation has been implicated in certain serious proliferative diseases such as lymphoma, cardiovascular disease, and nephrosclerosis. U.S. Pat. No. 5,639,600. Gabrielian et al. reported the role of macrophage infiltration in traumatic proliferative vitreoretinopathy. (1994) *Curr. Eye. Res.* 13:1-9. McGrath et al. disclosed the involvement of clonally expanded macrophages in the induction of cancerous tumor growth and AIDS dementia. U.S. Pat. Nos. 5,639,600 and 5,580,715; see also Pulliam et al. (1997) *Lancet* 349:692-695; McGrath et al. (1995) *J. Acquired Imm. Def. Syn. Hum. Retro.* 8: 379-385; Shiramizu et al. (1994) *Cancer Res.* 54:2069-2072.

AD is a degenerative brain disorder clinically characterized by progressive loss of memory, cognition, reasoning, judgment and emotional stability that gradually leads to profound mental deterioration and ultimately death. AD is a common cause of dementia in the elderly and is believed to represent the fourth most common medical cause of death in the United States. The disease is currently estimated to affect over four million Americans. To date, the disease is incurable. Various factors such as genetic predisposition, infectious agents, toxins, metals, and head trauma have all been suggested as possible mechanisms of AD neuropathy. A prevailing theory explaining the cause of AD is related to abnormal deposition of β-amyloid into plaques with associated neurofibrillary tangles. No HIV or other infectious agent has to date been associated with AD, and AD pathologic lesions are different than those associated with AIDS dementia.

Several different classes of chemical compounds have been reported that can inhibit abnormal cellular proliferation. These classes include, for example, anionic oligomers, amino 1,2,3-triazoles, valproic acid derivatives and polyamines. Cardin et al. reported that certain anionic oligomers possess antiproliferative activity. U.S. Pat. No. 5,460,807. Water soluble polyureas and polyamides with a molecular weight of less than 10,000 inhibit smooth muscle cell proliferation in culture and in vivo. Cardin et al. state that the anionic oligomers can be used in the treatment of atherosclerosis. Hupe et al. disclosed that certain triazoles are antiproliferatives. U.S. Pat. No. 4,847,257. Amino 1, 2, 3 triazoles inhibit labeled thymidine incorporation into intact pig skin and also inhibit keratinocyte proliferation. Hupe et al. state that the triazoles can be used in the treatment of psoriasis, a chronic skin disease which is characterized by hyperproliferation of the epidermis Nau et al. discovered that certain acids inhibit cell mitosis. U.S. Pat. No. 5,672,746. Derivatives of valproic acid decrease neuro-2a cell proliferation in vitro. Nau et al. state that the valproic acid derivatives can be used for the prevention and treatment of neurodegenerative disorders such as Alzheimer's disease. The treatment would be aimed at preventing the adverse effects of the disease by directly inhibiting pathologic neural cell growth.

The level of polyamines is intimately related to cell proliferation. Cellular levels of polyamines are carefully regulated by opposing synthetic and catabolic pathways. Compounds that are able to lower polyamine levels are proposed for use in the treatment of rapidly proliferating host cells such as cancer and psoriasis. A key polyamine catabolizing enzyme spermidine-spermine N1-acetyltransferase (SSAT) is among the few genes known to be inducible by the natural polyamines. Certain polyamine analogs exaggerate this response. 1,11-diethylnorspermine (DENSPM) increases SSAT mRNA levels in human melanoma cells up to 20-fold, with an increase in immunodetectable SSAT protein by 300-fold. By comparison, natural polyamine spermine is far less effective, increasing SSAT mRNA by ~3-fold and immunodetectable protein by ~7-fold. Fogel-Petrovic et al. (1996) *Biochemistry* 35:14435. Polyamine analogs also induce Z-DNA structure in vitro. This property correlates inversely with the effects on cis-diaminedichloroplatinum (II) (CDDP) cytotoxicity in human brain tumor cells. Basu et al. (1996) *Anticancer Res.* 16:39.

U.S. Pat. No. 5,498,522 outlines the use of SSAT as a prognostic indicator or tumor response marker. Either SSAT enzyme activity, SSAT enzyme protein, or mRNA transcripts can be measured directly, or other determinants related to SSAT induction can be measured, such as SSAT co-factor acetylCoA, and the SSAT products N1-acetylspermine and N1-acetylspermidine. Measurement of these determinants is proposed as a prognostic indicia and tumor response marker to evaluate the clinical effectiveness of anticancer agents comprising polyamine analogs. Determination is performed by collecting tumor cells by biopsy before or after treatment, and measuring the selected determinant. Hibasami et al. [(1989) *Cancer Res.* 49:2065] prepared an inhibitor of the natural polyamine synthetic pathway. The compound, methylglyoxal-bis(cyclopentylamidinohydrazone) (MGBCP) inhibited S-adenosylmethionine decarboxylase, spermine synthase, and spermine synthetase, competing with S-adenosylmethionine, spermidine, and putrescine, respectively. MGBCP depleted spermidine and spermine in leukemic ascites cells, and prolonged survival time of mice bearing P388 leukemia.

U.S. Pat. No. 5,541,230 (Basu et al.) indicates that spermine derivatives decrease growth in a number of human tumor cell lines, and propose their use in cancer chemotherapy. Bergeron et al. (*Cancer Chemother. Pharmacol.*) showed that the polyamine analogs 1,14-bis(ethylamino)-5,10-diazatetradecaone (BE-4-4-4), and 1,19-bis(ethylamino)-5,10,15-triazanonadecane (BE-4-4-4-4) directly affects growth, survival, and cell cycle progression in human brain tumor cell lines. The synthesis of BE-4-4-4-4 is disclosed in U.S. Pat. No. 5,541,230. U.S. Pat. No. 5,516,807 (Hupe et al.) claims a method for treating vascular proliferative disorders following balloon angioplasty. Bis-ethyl norspermine was found to inhibit the growth of rat aortic smooth muscle cells in culture for 8 to 15 days. It is proposed that restenosis following balloon angioplasty, graft, shunt, or athereotomy can be treated or prevented by administration of an effective amount of a polyamine, although no such experiments were performed. For other publications relating to the synthesis and use of certain polyamines, the reader is referred to EP 277,635, EP 162,413, EP 399,519, JP 85/6348, and U.S. Pat. No. 5,679,682; and to Bellevue et al. (1996) *Bioorg. Med. Chem. Lett.* 6:2765, and Porter et al. (1992) *Falk Symposium* 62:201; Marton and Pegg (1995) *Ann Rev. Pharmacol. Toxicol.* 35:55-91.

What is needed are methods of modulating macrophage proliferation that is associated with disease. There is also a need for methods of indicating development and/or progression of non-HIV-mediated dementias associated with macrophage proliferation.

All publications cited herein are hereby incorporated in their entirety.

DISCLOSURE OF THE INVENTION

The present invention provides methods for modulating macrophage proliferation using a composition comprising a polyamine analog or salt or protected derivative thereof (or using a polyamine analog or salt or protected derivative thereof), preferably in an individual afflicted with or at risk for a disease with which macrophage proliferation is associated, wherein the composition (or compound) is administered in an amount sufficient to modulate macrophage proliferation. In one embodiment, the disease is a non-HIV-associated dementia, particularly Alzheimer's disease. In another embodiment, the individual is HIV-infected and the disease is HIV-associated, such as HIV-associated dementia. Preferably, all the nitrogens of the polyamine analog are secondary, tertiary, or quaternary amino groups. The composition can further comprise a pharmaceutically acceptable excipient. In some embodiments, the composition comprises mitoguazone dihydrochloride.

In another aspect, the invention provides methods for modulating macrophage proliferation in an individual comprising administering a composition comprising an effective amount of an agent (or administering an effective amount of an agent) which interferes with polyamine interaction with a target in a proliferating macrophage, such as DNA, RNA, and/or membranes.

In another aspect, the invention provides methods of aiding diagnosis of a macrophage-associated dementia, particularly a non-HIV-associated dementia, including Alzheimer's disease (AD) an individual, comprising the step of detecting the presence of and/or the level of proliferating macrophages in the individual.

In another aspect, the invention provides methods of monitoring therapy of a macrophage-associated dementia, particularly a non HIV associated dementia, in an individual comprising detecting the presence of, and/or the level of, proliferating macrophages in a biological sample from the individual. The invention also includes methods of monitoring an individual at high risk of developing macrophage-associated, non-HIV associated dementia (such as AD), comprising detection of the presence of, or the level of, proliferating macrophages in a biological sample from that individual.

In another aspect, the invention provides methods of modulating macrophage proliferation in an individual afflicted with or at risk for Alzheimer's disease comprising administering to the individual a composition comprising a compound selected from the group consisting of a polyamine analog, a salt of a polyamine analog, and a protected derivative of a polyamine analog (or administering an effective amount of a compound selected from the group consisting of a polyamine analog, a salt of a polyamine analog, and a protected derivative of a polyamine analog), wherein all nitrogen atoms of said polyamine analog are secondary, tertiary, or quartenary amino groups, and where the composition (or compound) is administered in an amount sufficient to modulate macrophage proliferation in the individual.

In another aspect, the invention provides methods of modulating macrophage proliferation in an individual at afflicted with or at risk for a macrophage-associated non-HIV dementia (such as in a non-HIV infected individual) other than AD, comprising administering to the individual an effective amount of an agent that modulates macrophage proliferation (or a composition comprising an effective amount of an agent that modulates macrophage proliferation), wherein an effective amount is an amount sufficient to modulate macrophage proliferation. In some embodiments, the agent is a polyamine analog(s) as described herein.

In another aspect, the invention provides methods of delaying development of a macrophage-associated dementia other than AD in a non-HIV-infected individual comprising administering to an individual an effective amount of an agent that modulates macrophage proliferation (or administering a composition comprising an effective amount of the agent). The agent may be, for example, a polyamine analog.

MODES FOR CARRYING OUT THE INVENTION

Figure 1A:
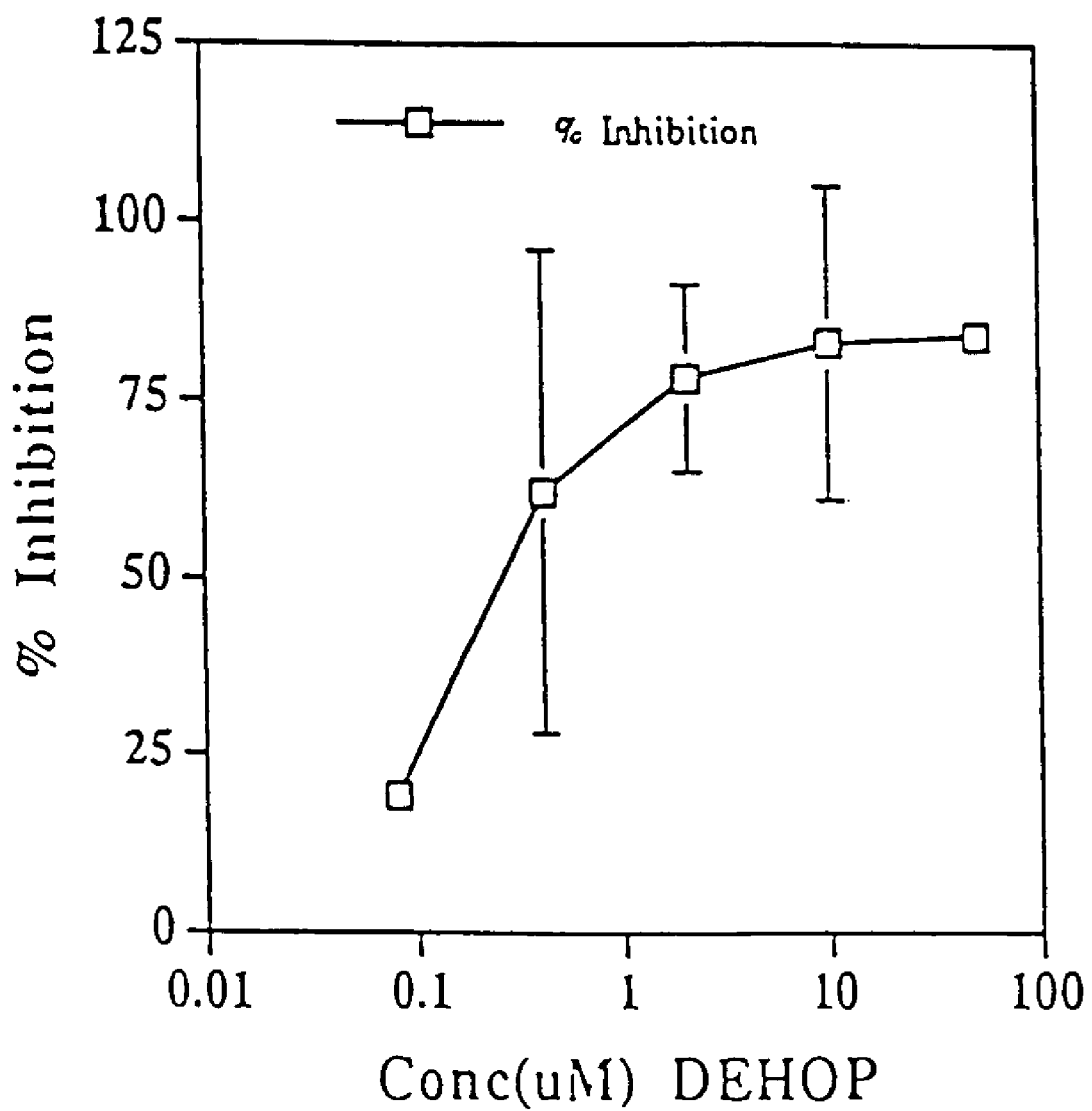
FIGS. 1A and 1B are graphs denoting percent inhibition or killing in vitro of macrophage proliferation by varying concentrations of polyamine analogs DEHOP (SunPharm) and BE-4444, compared to antineoplastic agent cyclosphosphamide. Blood was obtained from patients with AIDS dementia.

We have discovered that polyamine analogs are particularly effective in modulating macrophage proliferation. We have also discovered elevated, abnormal levels of macrophage proliferation in peripheral blood of patients with Alzheimer's disease (AD). We have also observed that macrophage proliferation is associated with a number of other serious disorders, including AIDS dementia, AIDS-associated non-Hodgkin's lymphoma, cardiovascular disease and nephrosclerosis. U.S. Pat. No. 5,639,600; see also commonly owned U.S. provisional application U.S. Ser. No. 60/063,318. Without wishing to be bound by a particular theory, we note that this macrophage proliferation phenomenon is associated with, and may contribute to the disease sequelae of, non-HIV associated dementias such as AD.

That polyamine analogs are effective in modulation of macrophage proliferation is evidenced by a polyamine analog-mediated decrease in proliferation marker PCNA (proliferating cell nuclear antigen) in CD14 expressing cells (i.e., macrophages). We have also observed that supernatants of proliferating macrophages are toxic to cells in the context of AIDS dementia, particularly brain cells. Controlling unwanted and harmful macrophage proliferation is thus a crucial aspect of developing new, effective treatment modalities for these disorders.

Accordingly, the invention provides methods for modulating macrophage proliferation, which are useful for controlling, palliating, and/or delaying development of these macrophage-proliferative disorders, including, but not limited to, certain neoplasms, HIV-associated diseases, and non-HIV associated dementias such as AD. The invention also provides methods of modulating macrophage proliferation in individuals afflicted with or at risk for a non-HIV associated dementia (as well as methods of delaying development of such dementia(s)), other than AD, which employ an agent which modulates macrophage proliferation (preferably a polyamine analog). The invention also provides methods of aiding diagnosis and/or monitoring therapy which entail measuring the presence of proliferating macrophages.

As discussed below, preferred agents for modulation of macrophages are polyamine analogs especially 1,11-bis(ethyl)norspermine; 1,8-bis(ethyl)spermidine (BES); 1,12-bis(ethyl)spermine (BESm; DESPM ($N^1,N^{12}$-diethylspermine); 1,11-bis(ethylamino)-4,8-diazaundecane (BE-3-3-3); 1,14-bis(ethylamino)-5,10-diazatetradecane (BE-4-4-4) (Diethylhomospermine, $N^1,N^{14}$-diethylhomospermine; DEHOP or DEHSPM); diethyl-norspermine (DENOP); 1,19-bis(ethylamino)-5,10,15-triazanonadecane (BE-4-4-4-4); N-ethyl-N'-(2-(3'-ethylamino-propylamino methyl)-cis-cyclopropylmethyl)-propane 1,3-diamine tetrahydrochloride (SL-11037); N-ethyl-N'-(2-(3'-ethylamino-propylamino methyl)-trans-cyclobutylmethyl)-propane 1,3-diamine tetrahydrochloride (SL-11038); N-ethyl-N'-(2-(3'-ethylamino-propylamino methyl)-trans-cyclopropylmethyl)-propane 1,3-diamine tetrahydrochloride (SL-11044; and N,N'-bis(3-ethylaminopropyl)-cis-but-2-ene-1,4-diamine tetrahydrochloride (SL-11047).

Definitions

As used herein, the terms "macrophage" and "monocyte" are used interchangeably, as it is understood that in the art the term "monocyte" is often used to describe a circulating mononuclear cell that expresses the CD14 cell surface marker, and when in a tissue this cell is also classified as a macrophage.

A "proliferating macrophage" is a term understood in the art and as used herein denotes a macrophage which is dividing. Normally a macrophage is a terminally differentiated cell incapable of further division. For purposes of this invention, a "proliferating macrophage" is capable of further division or is in a portion of the cell cycle not considered to be terminal or end stage. Preferably, the proliferation is clonal, i.e., is derived from a single cell. Methods of detecting proliferating macrophage(s) is discussed below.

As used herein, detecting the "presence of proliferating macrophages" generally means detecting the level of proliferating macrophages. It is understood that an absolute or even relative level need not be determined; an observation of detectable proliferating macrophages is sufficient.

A "macrophage-associated" disease, disorder or indication is a disease, disorder or indication that is associated with an elevated, or abnormal, level of macrophage proliferation as compared to control sample(s). Such disorders include, but are not limited to, AIDS-associated dementia, Alzheimer's disease (AD), AIDS lymphoma, follicular lymphoma, mycoses fungoides, T cell and B cell lymphomas with significant macrophage compartments, atherosclerosis, kidney disease such as focal segmental glomerulosclerosis and membrane proliferative glomerulo nephropathy, psoriaform dermatitities, AIDS-associated diarrhea, prelymphomatis autoimmune disease such as AILD (angioimmunoblastic lymphadenophathy with dysproteinemia) and herpes virus associated diseases such as Castleman's disease and Kaposi's sarcoma. The terms "disorder" and "disease" are used interchangeably herein. "Macrophage-associated dementia" is a dementia that is associated with an elevated, or abnormal, level of macrophage proliferation as compared to control sample(s). Such dementias include, but are not limited to, AD. A macrophage-associated disorder, disease or dementia can be HIV-mediated or non-HIV-mediated, or HIV-associated or non-HIV associated. A "non-HIV-mediated" disease or dementia is a disease or dementia which is not caused by HIV, either directly or indirectly. A "non-HIV-associated" disease or dementia is a disease or dementia not normally associated with or secondary to HIV infection. An "HIV-mediated" disease, dementia or indication is directly or indirectly caused by (and/or linked to) HIV infection. An "HIV-associated" disease, dementia or indication is defined more broadly as generally associated with or secondary to an HIV infection; "HIV-mediated" diseases, for example, are included in those considered to be "HIV-associated."

An individual "afflicted with" a macrophage associated disorder or non-HIV associated dementia means that the individual individual has been diagnosed as having, or is suspected as having, a macrophage associated disoreder or a non-HIV associated dementia.

By a "polyamine", a term well-understood in the art, is meant any of a group of aliphatic, straight-chain amines derived biosynthetically from amino acids; polyamines are reviewed in Marton et al. (1995) *Ann. Rev. Pharm. Toxicol.* 35:55-91. By "polyamine" is generally meant a naturally-occurring polyamine or natural polyamine, which are naturally produced in eukaryotic cells. Examples of polyamines include putrescine, spermidine, spermine and cadaverine.

By "polyamine analog" is meant an organic cation structurally similar but non-identical to naturally-occurring polyamines such as spermine and/or spermidine and their precursor, diamine putrescine. Polyamine analogs can be branched or un-branched, or incorporate cyclic moieties. Examples of polyamine analogs include, without limitation, $N^1$, $N^{14}$-diethylhomo-spermine (DEHSPM) and $N^1$,$N^{12}$-diethylspermine (DESPM). See, for example, WO 98/17624 and U.S. Pat. No. 5,541,230. U.S. Pat. Nos. 5,037,846 and 5,242,947 disclose polyamines comprising primary amino groups. Especially preferred are polyamine analogs wherein all nitrogen atoms of said polyamine analogs are independently secondary, tertiary, or quarternary amino groups.

An "alkyl" is a cyclic, branched, or straight chain chemical group containing carbon and hydrogen, such as methyl, butyl, t-butyl, pentyl, cyclopropyl, and octyl. Alkyl groups can be either unsubstituted or substituted with one or more substituents, e.g., halogen, alkoxy, acyloxy, amino, hydroxyl, mercapto, carboxy, benzyl. Alkyl groups can be saturated or unsaturated (e.g., containing —C=C— or —C≡C— subunits), at one or several positions. Unless otherwise specified, alkyl groups will comprise 1 to 8 carbon atoms, preferably 1 to 6, and more preferably 1 to 4 carbon atoms. "Cycloalkyl" refers to cyclic alkyl groups only, such as cyclopropyl, cyclobutyl, cyclopentyl, etc. "n-alkyl" refers to a linear (i.e., straight-chain) alkyl group only, while "branched alkyl" refers to branched alkyl groups to the exclusion of cyclic and linear alkyl groups. "Alkenyl" refers to a cyclic, branched, or straight chain chemical group containing carbon and hydrogen where at least one bond is monounsaturated, such as ethenyl, cyclopentenyl, or 1,3-butadienyl. Alkenyl groups can be substituted as indicated for alkyl groups. Alkenyl groups can be designated as cyclic, linear (n-alkenyl) or branched in an analogous fashion to the preceding designations for alkyl. An "aryl" is an unsaturated aromatic carbocyclic group having a single ring (e.g., phenyl), or multiple condensed rings (e.g., naphthyl), which can optionally be unsubstituted or substituted with amino, hydroxyl, alkyl, alkoxy, chloro, halo, mercapto and other substituents.

A "stereoisomer" is defined as any optical isomer of a compound, including enantiomers and diastereomers. Unless otherwise indicated, structural formula of compounds are intended to embrace all possible stereoisomers.

A "salt" is defined as a compound formed by the replacement of one or more hydrogen atoms with elements or groups, which is composed of anions and cations, which usually ionizes in water; a salt is formed, for instance, by neutralization of an acid by a base. A polyamine analog salt can comprise, for example, chloride ions.

"Protected derivative" is used to refer to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Exemplary protecting groups for the amino functionality include, but are not limited to, mesitylenesulfonyl ($MesSO_2$), benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc).

An "individual" is a vertebrate, preferably a mammal, more preferably a human. Mammals include, but are not limited to, farm animals, sport animals, rodents, primates, and pets. A "non-HIV-infected individual" is an individual who has not been infected by HIV. An "HIV-infected" individual may or may not yet display clinical manifestations of infection. HIV and methods of detecting HIV infection are well known in the art and need not be discussed herein.

As used herein, "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples. Generally, the sample will be, or be derived from, peripheral blood. Preferably, the blood will have been enriched for a macrophage fraction, by using, for example, glass or plastic adherence.

As used herein, "aiding diagnosis" means that these methods assist in making a clinical determination regarding the classification, or nature, of the dementia, and may or may not be conclusive with respect to the definitive diagnosis. The method of aiding diagnosis of a macrophage-associated disease can comprise the step of detecting the level of proliferating macrophages in a biological sample from the individual, wherein the disease is dementia, such as a non-HIV-associated dementia, such as Alzheimer's disease. Dementias may or may not be associated with clonal macrophage proliferation, and making this classification may assist in developing and recommending treatment strategies as well as evaluating prognosis.

"Development" of a dementia herein means initial manifestations and/or ensuing progression of the disorder. Development of disease can be detectable and assessed using standard clinical techniques, such as neurofunction/cognitive tests and brain scanning technologies such as MRI. However, development also refers to disease progression that may be undetectable. For purposes of this invention, progression refers to the biological course of the disease state. "Development" includes occurrence, recurrence, and onset. As used herein "onset" or "occurrence" of a neurological disorder includes initial onset and/or recurrence. As used herein, "delaying" development of disease means to defer, hinder, slow, retard, stabilize, and/or postpone development of the disease. This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of disease is a method that reduces the extent of the disease in a given time frame, when compared to not using the method. Such comparisons are typically based on clinical studies, using a statistically significant number of subjects, although this knowledge can be based upon anecdotal evidence. "Delaying development" can mean that the extent and/or undesirable clinical manifestations are lessened and/or time course of the progression is slowed or lengthened, as compared to not administering the agent. Thus the term also includes, but is not limited to, alleviation of symptoms, diminishment of extent of disease, stabilized (i.e., not worsening) state of disease, delay or slowing of disease progression, and remission (whether partial or total) whether detectable or undetectable.

As used herein, an "effective amount" (e.g., of an agent) is an amount (of the agent) that produces a desired and/or beneficial result. An effective amount can be administered in one or more administrations. For purposes of this invention, an effective amount is an amount sufficient to produce modulation of macrophage proliferation. An "amount (of a polyamine analog) sufficient to modulate macrophage proliferation" preferably is able to alter the rate of proliferation of macrophages by at least 25%, preferably at least 50%, more preferably at least 75%, and even more preferably at least 90%.

Such modulation may have desirable concomitant effects, such as to palliate, ameliorate, stabilize, reverse, slow or delay progression of disease, delay or even prevent onset of disease.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds, such as plant or animal extracts, and the like. Agents include, but are not limited to, polyamine analogs. Agents can be administered alone or in various combinations.

"Modulating" macrophage proliferation means that the rate of proliferation is altered when compared to not administering an agent that interferes with natural polyamine interaction with DNA (including, but not limited to, interfering with a polyamine biosynthetic pathway, interfering with the intracellular concentration of spermidine, competitors, inhibitors of DNA interaction by a natural polyamine, interfering with polyamine metabolism, etc.), such as a polyamine analog. Preferably, "modulating" macrophage proliferation means a change in the rate of macrophage proliferation of at least 25%, preferably at least 50%, more preferably at least 75%, and even more preferably at least 90%. Generally, for purposes of this invention, "modulating" macrophage proliferation means that the rate of proliferation is decreased when compared to the rate of proliferation in that individual when no agent is administered. However, during the course of therapy, for example, it may be desirable to increase the rate of proliferation from a previously measured level. The degree of modulation may be assessed by measurement of macrophage proliferation, which will be discussed below, and generally entails detecting a proliferation marker(s) in a macrophage population or uptake of certain substances such as BrdU or $^3$H-thymidine (which would provide a quantitative measure of proliferation). Further, it is possible that, if the macrophages are proliferating due to a genetic alteration (such as transposition, deletion, or insertion), this alteration could be detected using standard techniques in the art, such as RFLP (restriction fragment length polymorphism).

A "target" of a polyamine or polyamine analog is an entity which interacts, either directly or indirectly, with the polyamine or polyamine analog(s). Examples of targets are DNA, RNA, and/or membranes.

Methods of the Invention

The invention provides methods for modulating macrophage proliferation in an individual afflicted with or at risk for a macrophage-associated disease comprising administering a polyamine analog, a salt of a polyamine analog, or a protected derivative of a polyamine analog, in an amount sufficient to modulate macrophage proliferation in the individual (i.e., an effective amount). Alternatively, a composition comprising a polyamine analog, or a protected derivative of a polyamine analog is administered in an amount sufficient to modulate macrophage proliferation (i.e., an effective amount). Examples of macrophage-associated diseases have been described above, and include, but are not limited to, HIV-associated diseases (i.e., in an HIV-infected individual) such as HIV associated dementia, non HIV associated dementias (such as AD), and certain neoplasms. Polyamine analogs are discussed below.

For purposes of this invention, an individual suitable for administration of a polyamine analog (or, in certain contexts, such as non-HIV associated dementia other than AD, an agent which modulates macrophage proliferation) is one who has been diagnosed as having a macrophage-associated disorder, such as AIDS dementia, AIDS non-Hodgkin's lymphoma, Alzheimer's disease, or who is adjudged to be at high risk for developing such a disorder. In some embodiments, an individual suitable for administration of an agent which modulates macrophage proliferation is one who has been diagnosed as having a macrophage-associated, non HIV associated dementia other than AD, or who is adjudged to be at risk for developing such a dementia. As is evident to one skilled in the art, these methods can apply to those individuals not displaying any symptoms. An "at risk" or "high risk" individual is an individual who has a discrete and significant risk of developing disease (a macrophage-associated disorder). An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, genetic (i.e., hereditary) considerations (including family history and genetic markers), and presence or absence of appropriate chemical markers and exposure to environments, conditions, or factors which would increase the possibility of acquiring a particular disease. Retroviral infections, especially retroviral insertions into particular genetic loci (such as fur or PDGF), may also be considered a risk factor. A high risk individual has one, preferably two, more preferably three, risk factors. However, it is understood that having only one risk factor can often indicate high risk.

Because all risk factors for developing macrophage-associated disease are not known, and the interplay among these factors (in terms of overall risk) are not fully understood, it is clear to one skilled in the art that individuals suitable for administration of an agent for purposes of this invention can have clinical features in common, and that individuals not falling clearly in the categories described above can nonetheless be considered suitable candidates for administration of an agent. For example, an individual having a genetic marker for development of a neurodegenerative disorder (such as the apoE gene) could be considered at risk for developing Alzheimer's disease, even though no previous disease has been observed. In this context, administration of an agent to such an individual could result in delay of occurrence of disease, even to the extent that the individual does not develop AD within his or her lifetime (or develops it later than would have been expected). Another example is an individual who is being treated using other modes of therapy, and who is showing clinical responsiveness to the therapy (i.e., stabilization or remission). Such an individual may be adjudged as at "high risk" even though the initial course of therapy is not yet completed, due to projection of clinical progress by the clinician, and can be a suitable candidate for receiving an agent before completion of the initial therapy. The clinician, as one skilled in the art, has discretion to determine whether treatment using an agent may be indicated.

In another embodiment, the invention provides methods for modulating macrophage proliferation in an individual (who is generally afflicted with or at risk of for a macrophage associated disease) comprising administering a composition comprising an effective amount of an agent that interferes with polyamine interaction with proliferating macrophage target, such as DNA, RNA, and/or membranes. An agent that interferes with polyamine interaction with a proliferating macrophage target(s) is one which interferes with any aspect of natural polyamine synthesis and/or metabolism, intracellular concentration regulation, and/or function (i.e., interaction with DNA).

The present invention further provides methods for aiding in the diagnosis of or monitoring therapy in individuals having a macrophage-associated disease, wherein the disease is a non-HIV associated dementia, such as AD. These methods comprise detecting the presence of proliferating macrophages in a biological sample from the individual.

In those individuals considered at high or significant risk of developing dementia, detection of proliferating macrophages in a biological sample may also assist in alerting the individual and/or the clinician of possible precursor disease. Thus, the invention also includes methods of monitoring an individual at risk or high risk of developing dementia, comprising detection of proliferating macrophages in a biological sample from that individual. Preferably, the individual is "afflicted with" (e.g., diagnosed as having, suffering from and/or displaying one or more clinical symptoms of) a particular disease, disorder or indication, or at "risk" for (e.g., having a genetic predisposition for, or family history of, or being environmentally exposed to factors which increase the probability of acquiring) a particular disease, disorder, or indication.

In another embodiment, the invention provides methods of monitoring therapy of a macrophage-associated dementia, which is a non-HIV associated dementia, such as AD, in an individual (who is generally not infected with HIV, although it is possible to develop a non-HIV associated dementia in an individual who is also infected with HIV) comprising detecting the presence of (i.e., the level of) proliferating macrophages in a biological sample. As the level of macrophage proliferation is associated with these conditions, monitoring these levels may in turn indicate initial responsiveness and efficacy, as well as the appropriate dosage of the therapy. It is understood that monitoring therapy or an individual at (high) risk means that biological sample(s) are obtained at different times, for example, during application of therapy, and are compared, either with each other, a control, and/or a desired value. In one embodiment, monitoring therapy includes the step of detecting macrophage proliferation.

Detection of proliferating macrophage(s) can be achieved using any of several techniques. In some embodiments of the invention, proliferation is measured in relation to circulating macrophages, and is performed on a leukocyte preparation from peripheral blood. In other embodiments of the invention, proliferation is measured in relation to tissue-fixed macrophages, typically performed on tissue sections. Proliferating macrophages may be detected, for example, by assaying cell proliferative markers, such as PCNA, Ki67 or uptake of bromodeoxyuridine (BrdU) or $^3$H-thymidine. These markers are distinct from those that identify only "activated" macrophages (as opposed to proliferating macrophages), such as CD69 and CD25. The cellular subset representing macrophages may in turn be identified by detection of certain cell specific markers, such as CD14, CD68, CD16, or nonspecific esterase. Detection of these cell-type and/or proliferative markers use methods standard in the art, such as staining techniques and FACS sorting and analysis. These methods are further described in Example 1. Further, it is possible that these proliferating macrophages could be distinguished based on other characteristics, such as cell density (as measured in PERCOLL™ gradients, for example). These determinations may be established empirically using standard techniques in the art.

For the purpose of aiding in the diagnosis of or predicting a macrophage-associated non-HIV associated dementia, the level of proliferating macrophages in a sample is generally compared with the mean or median level in samples taken from healthy individuals, matched where necessary for sex and age. The level can be calculated as the absolute number of proliferating macrophages obtained from a blood sample (or detected by immunohistopathology of a tissue section). More usually, the level is calculated as a percentage of total macrophages in the sample, identifiable by cell markers or morphological characteristics, since this normalizes for differences in the number of macrophage-like cells recovered in the sample.

As with many clinical tests, a finding of about three standard deviations above the average is statistically significant and indicates an abnormality. A finding of one or two standard deviations above the average is reason for concern. In combination with other indicators, an elevated level may aid in diagnosis of dementia, or some other condition associated with macrophage proliferation. For example, peripheral blood leukocytes stained and counted for PCNA/CD14 cells are consistent with macrophage-associated dementia in the individual if the percentage of positively stained cells is above 50%, more strongly suggests macrophage-associated dementia if above about 75%, and even more strongly suggestive of macrophage-associated dementia if above about 90%. The differential diagnosis will include any condition associated with macrophage proliferation as a causative or consequential effect, with the ultimate diagnosis being the responsibility of the managing physician or clinician.

For the purpose of monitoring the effect of a macrophage proliferation inhibitor, the level of proliferating macrophages in a treated sample is generally compared with the level in an untreated sample. For the general screening of proliferation inhibitors, peripheral blood leukocytes are isolated from an individual affected with a disease associated with proliferating macrophages. Samples of the cells are treated with the candidate compound, and the effect is compared with cells not treated. When administered to a patient, the effect of a macrophage proliferation inhibitor is determined by comparing the level of proliferating macrophages before and during treatment, with a downward trend generally being consistent with a positive effect.

In another embodiment, the invention provides methods of delaying development of a macrophage-associated dementia other than AD, in a non-HIV-infected individual (i.e., a non HIV associated dementia other than AD). These methods comprise administration of an effective amount of an agent which modulates macrophage proliferation to the individual. Such agents, which include polyamine analogs (including stereoisomers, their salts, and protected derivatives thereof), are described below. The invention also includes methods of treatment or palliation of these disorders using an agent(s) which modulates macrophage proliferation.

Agents for Modulating Macrophage Proliferation

In some embodiments of the invention, macrophage proliferation is accomplished by using a polyamine analog (including stereoisomers, salts, and protected derivatives thereof). In other embodiments, more particularly, those which involve a non-HIV associated dementia other than AD, any agent which modulates macrophage proliferation may be used. With respect to polyamine analogs, it is understood that the discussion also applies to stereoisomers, salts and protected derivatives thereof.

Polyamine Analogs

The polyamine analogs used in the present invention include compounds of the structures 1, 2, 3, 4, and 5, and the corresponding stereoisomers, salts, and protected derivatives thereof:

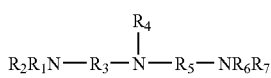

1 where $R_1$, $R_2$, $R_4$, $R_6$ and $R_7$ are independently selected from the group consisting of hydrogen, alkyl and aryl, and where $R_3$ and $R_5$ are alkyl groups;

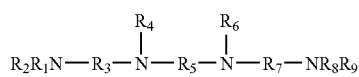

2 where $R_1$, $R_2$, $R_4$, $R_6$, $R_8$, and $R_9$ are independently selected from the group consisting of hydrogen, alkyl and aryl, and where $R_3$, $R_5$ and $R_7$ are alkyl groups;

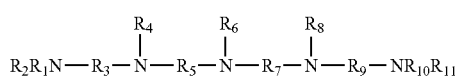

3 where $R_1$, $R_2$, $R_4$, $R_6$, $R_8$, $R_{10}$ and $R_{11}$ are independently selected from the group consisting of hydrogen, alkyl and aryl, and where $R_3$, $R_5$, $R_7$ and $R_9$ are alkyl groups;

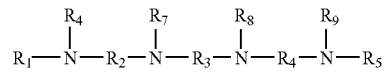

4 where $R_1$ and $R_5$ are independently selected from the group consisting of methyl, ethyl, n-propyl, and isopropyl;
where $R_2$, $R_3$, and $R_4$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl;
and where $R_6$, $R_7$, $R_8$ and $R_9$ are independently selected from the group consisting of H, methyl, and ethyl;

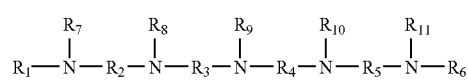

5 where $R_1$ and $R_6$ are independently selected from the group consisting of methyl, ethyl, n-propyl, and isopropyl;
where $R_2$, $R_3$, $R_4$ and $R_5$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl $C_3$-$C_{10}$ aryl, and $C_1$-$C_6$ alkyl-$C_3$-$C_{10}$-aryl-$C_1$-$C_6$ alkyl;
and where $R_7$, $R_8$, $R_9$, $R_{10}$ and $R_{11}$ are independently selected from the group consisting of H, methyl, and ethyl.

Preferably, the polyamine analogs will include compounds of the structures 2 and 3, where $R_3$, $R_5$, $R_7$ and $R_9$ are independently $(CH_2)_x$ groups, where x is an integer from 2 to 6, and further where $R_4$, $R_6$ and $R_8$ are hydrogen atoms.

More preferably, the polyamine analogs will include compounds of the structures 2 and 3, where $R_3$, $R_5$, $R_7$ and $R_9$ are independently $(CH_2)_x$ groups, where x is an integer from 2 to 6, and where $R_4$, $R_6$ and $R_8$ are hydrogen atoms, and where $R_1$ and $R_{10}$ are alkyl groups, and further where $R_2$ and $R_{11}$ are hydrogen atoms.

Most preferably, the polyamine analogs will include compounds of the structures 2 and 3, where $R_3$, $R_5$, $R_7$ and $R_9$ are independently $(CH_2)_x$ groups, where x is an integer from 2 to 6, and where $R_4$, $R_6$ and $R_8$ are hydrogen atoms, and where $R_1$ and $R_{10}$ are alkyl groups, and where $R_2$ and $R_{11}$ are hydrogen atoms, and further where the polyamine analogs have a molecular weight less than 500.

Additional preferred compounds also include compounds of the structure 4,
where $R_6$, $R_7$, $R_8$ and $R_9$ are H;
where $R_1$ and $R_5$ are ethyl;
where $R_6$, $R_7$, $R_8$ and $R_9$ are H and $R_1$ and $R_5$ are ethyl;
and/or where $R_2$ and $R_4$ are independently selected from the group consisting of $C_1$-$C_6$ alkyl and $R_3$ is selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl.

Additional polyamine analogs useful in the present invention include compounds of the formula 6, and the corresponding stereoisomers, salts, and protected derivatives thereof:

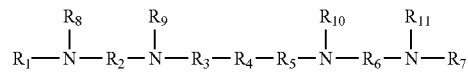

6 where $R_4$ is $C_2$-$C_6$ n-alkenyl, $C_3$-$C_6$ cycloalkyl, $C_3$-$C_6$ cycloalkenyl, or $C_3$-$C_6$ aryl;

$R_3$ and $R_5$ are independently chosen from a single bond, $C_1$-$C_6$ alkyl, or $C_1$-$C_6$ alkenyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are H.

In preferred embodiments of the compounds of formula 6, $R_1$ and $R_7$ are independently chosen from $C_1$-$C_6$ alkyl or $C_2$-$C_6$ alkenyl.

Additional polyamine analogs useful in the present invention include compounds of the formula 7, and the corresponding stereoisomers, salts, and protected derivatives thereof:

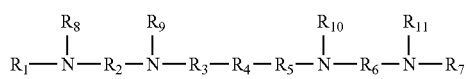

7 where $R_4$ is $C_1$-$C_6$ n-alkyl or $C_1$-$C_6$ branched alkyl;

$R_3$ and $R_5$ are independently chosen from a single bond or $C_1$-$C_6$ alkyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are H.

In preferred embodiments of the compounds of formula 7, $R_1$ and $R_7$ are independently chosen from $C_1$-$C_6$ alkyl or $C_2$-$C_6$ alkenyl, $R_4$ is $C_1$-$C_6$ saturated n-alkyl or $C_1$-$C_6$ saturated branched alkyl, and $R_3$ and $R_5$ are independently chosen from a single bond or $C_1$-$C_6$ saturated n-alkyl.

When compounds of formulas 1-7 contain terminal primary amino groups (that is, in compounds of formula 1, when $R_1$ and $R_2$ are both H, and/or $R_6$ and $R_7$ are both H; in compounds of formula 2, when $R_1$ and $R_2$ are both H, and/or $R_8$ and $R_9$ are both H; in compounds of formula 3, when $R_1$ and $R_2$ are both H, and/or $R_{10}$ and $R_{11}$ are both H; in compounds of formula 4, when $R_1$ and $R_6$ are both H, and/or $R_5$ and $R_9$ are both H; in compounds of formula 5, when $R_1$ and $R_7$ are both H, and/or $R_6$ and $R_{11}$ are both H; in compounds of formula 6, when $R_1$ and $R_8$ are both H, and/or $R_7$ and $R_{11}$ are both H; in compounds of formula 7, when $R_1$ and $R_8$ are both H, and/or $R_7$ and $R_{11}$ are both H), the diseases treated with such compounds include all diseases disclosed herein except Alzheimer's disease.

Preferably, all the nitrogens of the polyamine analog are independently secondary, tertiary, or quaternary amino groups.

Among polyamine analogs preferred for use in this invention are those compounds with a demonstrated ability to modulate naturally occurring polyamine levels in cells. Without intending to be limited by theory, possible mechanisms include competition in the polyamine synthesis pathway; upregulation of polyamine catabolizers such as SSAT; affecting polyamine metabolism.

Of special interest are the following polyamine analogs:

1,11-bis(ethyl)norspermine (1,11-bis(ethylamino)-4,8-diazaundecane; BE-3-3-3)

1,8-bis(ethyl)spermidine (BES)

1,12-bis(ethyl)spermine (BESm; DESPM ($N^1$,$N^{12}$-diethylspermine; SunPharm);

1,14-bis(ethylamino)-5,10-diazatetradecane (BE-4-4-4) (Diethylhomospermine, $N^1$,$N^{14}$-diethylhomospermine; DEHOP or DEHSPM; SunPharm)

diethyl-norspermine (DENOP; SunPharm)

1,19-bis(ethylamino)-5,10,15-triazanonadecane (BE-4-4-4-4)

N-ethyl-N'-(2-(3'-ethylamino-propylamino methyl)-cis-cyclopropylmethyl)-propane 1,3-diamine tetrahydrochloride (SL-11037), provided by S'LIL, Madison, Wis.

N-ethyl-N'-(2-(3'-ethylamino-propylamino methyl)-trans-cyclobutylmethyl)-propane 1,3-diamine tetrahydrochloride (SL-11038), S'LIL N-ethyl-N'-(2-(3'-ethylamino-propylamino methyl)-trans-cyclopropylmethyl)-propane 1,3-diamine tetrahydrochloride (SL-11044), S'LIL.

N,N'-bis(3-ethylaminopropyl)-cis-but-2-ene-1,4-diamine tetrahydrochloride (SL-11047), S'LIL The structures of SL-11037, SL-11038, SL-11044, and SL-11047 are diagrammed below:

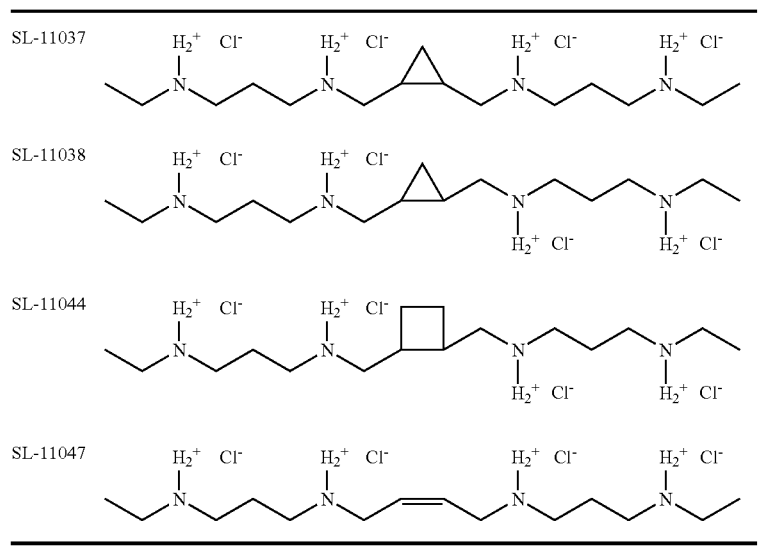

Besides the polyamine analogs listed above, stereoisomers, salts or protected derivatives thereof, may be used. The invention also comprises methods of using an effective amount of any of the polyamine analogs listed above, or stereoisomers, salts or protected derivatives thereof (or a composition comprising an effective amount of any of the polyamine analogs listed above, or stereoisomers, salts or protected derivatives thereof) in modulating macrophage proliferation (or in treating or delaying development of macrophage-associated diseases, including HIV-associated dementia and AD). The invention also comprises any polyamine analog listed above, or stereoisomers, salts or protected derivatives thereof, for use in preparing compositions (i.e., medicaments) useful for treating macrophage-associated diseases, including HIV-associated dementia, and Alzheimer's disease.

Any polyamine analog listed above, or stereoisomers, salts or protected derivatives thereof (or a composition comprising an effective amount of any polyamine analog listed above, or stereoisomers, salts or protected derivatives thereof) may be used in vitro or in vivo. In vitro, a suitable biological sample (such as a blood sample, which may or may not be enriched for the macrophage population) is contacted with the composition(s). In vivo, a composition of the invention is generally administered according to the manufacturer's/supplier's instructions. Generally, polyamine analogs are administered by subcutaneous or intravenous injection. They may also be administered orally.

The amount of a polyamine analog (or stereoisomers, salts or protected derivatives thereof) administered will depend on several variables, such as the particular analog (or sterioisomer, salt or protective derivative) used, the time course of administration, the condition of the individual, the desired objective, the extent of disease, how many doses will be administered, and whether any other substances are being administered. Generally, the amount used will be as recommended by the manufacturer and/or based on empirical studies. In the case of polyamine analogs (or stereoisomer, salt, or protected derivative thereof), the amount will generally be between about 1 to about 300 mg/m$^2$/day, possibly between about 15 to about 150 mg/m$^2$/day. Administration is generally intermittant, meaning that analog (or stereoisomer, salt, or protected derivative thereof) is administered per a period of at least one to two days and then not administered for a period of at least one to two days, with the cycle repeated as indicated. In one embodiment, the polyamine analog (or stereoisomer, salt, or derivative thereof) for 6 days every three weeks.

Routes of administration will generally depend on the nature of the particular polyamine analog (or stereoisomer, salt or protective derivative) used, and may be, for example, oral or by injection (subcutaneous or intravenous). Administration is generally by intravenous or subcutaneous injection.

Preferably, a polyamine analog (or stereoisomer, salt or protected derivative), or other suitable agent that interferes with the polyamine synthetic pathway, polyamine metabolism, and/or the intracellular concentration maintenance of spermine) is administered in a suitable pharmaceutical excipient. Pharmaceutical excipients are known in the art and are set forth in *Remington's' Pharmaceutical Sciences*, 18th edition, Mack Publishing (1990). The polyamine analog may also be associated with another substance that facilitates agent delivery to macrophages, or increases specificity of the agent to macrophages. For example, an agent(s) may be associated into liposomes. Liposomes are known in the art.

The liposomes in turn may be conjugated with targeting substance(s), such as IgGFc receptors. Substances that increase macrophage phagocytosis such as zymosan or tetrachlorodecaoxygen (TCDO) and/or activation such as MCSF, GMCSF or IL-3 may be used to increase uptake of anti-proliferative agent(s).

A polyamine analog (or stereoisomer, salt or protected derivative) may be administered alone, or in conjunction with other substances and/or therapies, depending on the context of administration (i.e., desired end result, condition of the individual, and indications). "In conjunction with" means that an agent is administered prior to, concurrently, or after other substance or therapy. Examples of substances that might be administered in conjunction with an agent include, but are not limited to, brain neurochemical modulators (in the context of macrophage-associated dementias), and classic anti-neoplastic agents and/or anti-lymphocytic agents such as steroids and cyclosporine derivatives. For example, a polyamine analog (or a stereoisomer, salt or protected derivative thereof) can be administered in conjunction with mitoguazone dihydrochloride.

The mechanistic effectiveness of various polyamine analogs and enzyme inhibitors can be determined at least in part by their ability to deplete intracellular polyamine pools. Kramer et al. [(1995) *Biochem. Pharmacol.* 50:1433[describe the use of 4-fluoro-L-ornithine to monitor metabolic flux through the polyamine biosynthetic pathway. It was determined that the metabolic flux indicated by the rate of appearance of fluorinated polyamines, reflected the proliferation status of the cells. U.S. Pat. No. 5,498,522 outlines the use of SSAT as a prognostic indicator or tumor response marker. Either SSAT enzyme activity, SSAT enzyme protein, or mRNA transcripts can be measured directly, or other determinants related to SSAT induction can be measured, such as SSAT co-factor acetylCoA, and the SSAT products N1-acetylspermine and N1-acetylspermidine. To further determine the effect of a polyamine analog's administration, an individual may be monitored for disease (or precursor disease) progression as well as biochemical and/or genetic markers of disease (or precursor disease). With respect to disease progression, multiple rating scales (i.e., indices of clinical function) have been established and are known in the art for various macrophage proliferative disorders such as AD and lymphomas. For macrophage-associated neurological disorders, cognitive functions can be tested and, in some cases, imaging modalities such as MRI may be used.

Other Agents for Modulating Macrophage Proliferation

Besides the polyamine analogs described above, suitable agents for use in modulating macrophages in the context of non-HIV associated dementias other than AD, include general anti-proliferative agents (i.e., proliferation-modulating agents). These include, but are not limited to, daunomycin, mitomycin C, daunrorubicin, doxorubicin, 5-FU, cytocine arabinoside, colchicine, cytochalasin B, bleomycin, vincristin, vinblastine, methotrexate, cis platinum, ricin, abrin, diphtheria toxin, and saporin.

Other suitable agents would be those which inhibit, or interfere with, the polyamine synthetic pathway, or those which affect the metabolism of polyamines. Other suitable agents are those which affect the closely regulated intracellular concentration of spermidine. An example of such an agent is MGBG (mitoguazone dihydrochloride; XYRKAMINE®; Ilex, Tex.) which inhibits S-adenosylmethionine decarboxylase which in turn is required for the production of polyamines. Any agent that interferes with polyamine interactions with proliferating macrophage target, such as DNA, RNA, and/or membranes would likewise be suitable. Another type of useful agent is one that interferes with polyamine interactions with DNA. Such an agent(s) could exert this function, for example, by any of the effects above (i.e., interfering with the polyamine synthetic pathway and/or metabolism, disturbing the concentration of intracellular spermine, competitors, etc.) as well as affecting polyamine function in terms of interacting with DNA. It is understood that, with respect to these and any other agent described herein, toxicology considerations also must be taken into account when determining whether, and/or in what amount, an agent is to be used.

It is understood that, with respect to the above-described agents, some can reasonably be considered as, and are considered as, polyamine analogs. An example is MGBG.

Administration and other considerations have been described above.

The following examples are provided to illustrate but not limit the invention.

EXAMPLES

Example 1

Testing Various Polyamine Analogs for Effect on Macrophage Proliferation in the Context of Macrophage-Associated Disorders Separation of Peripheral Blood Monocytes We had previously separated peripheral blood monocytes on Ficoll. We found that a standard Ficoll Hypaque separation gave lower yields of monocytes from demented patients than from HIV-infected controls (44 vs 67%, respectively). Several demented patients yielded under 10% of predicted, suggesting that a subset of monocytes was being missed. We then used Percoll gradient separation, which allows for denser cells to be captured. A two-step gradient was prepared in 15 mL conical tubes: bottom layer of 1.087 density Percoll, overlaid with 1.077 density. 1.5 mL whole heparinised blood was mixed with an equal volume of isotonic saline. This blood/saline was layered over the gradient and centrifuged. Cells from the 1.077 and 1.087 interfaces were collected, combined, and washed in 5 volumes of RPMI 1640. Specimens from patients with macrophage proliferative diseases such as AIDS dementia had a high frequency of dense (1.087 g/cc) monocytes. All further experiments were performed using 1.087 gradient.

Five×$10^5$ PBMC's isolated through a 1.087 g/cc Percoll/saline gradient were exposed to varied concentrations of agent after baseline CD14/PCNA staining was performed. The cells were cultured at 5×$10^5$ cells in RPM1-1640/10% fetal calf serum in a polypropylene tube (Falcon) at 37° C. for five days. After five days CD14/PCNA staining was performed on control and agent-treated cultures. FACSCAN analysis of PCNA-positive cells in control cultures was compared with agent-treated cultures and the percentage of control PCNA/CD14 cells was calculated. The results of such an experiment in which the effect of polyamine analog DEHOP (SunPharm; Florida) on proliferating macrophages (as detected by PCNA) from the blood of four patients with AIDS dementia are shown in FIG. 1A (with underlying data provided in Table 3). This polyamine analog significantly reduced the percentage of proliferating macrophages. A comparison of the inhibitory effect of DEHOP and cyclophosphamide, another anti-proliferative agent, was performed in vitro using the blood of one of these patients ("CB"). The results are shown in Table 1. This experiment showed that DEHOP was superior in inhibition. This polyamine analog effect is relative and specific as indicated by a lack of in vitro toxicity in this assay system by cyclophosphamide, a classic anti-neoplastic agent.

Figure 1B:
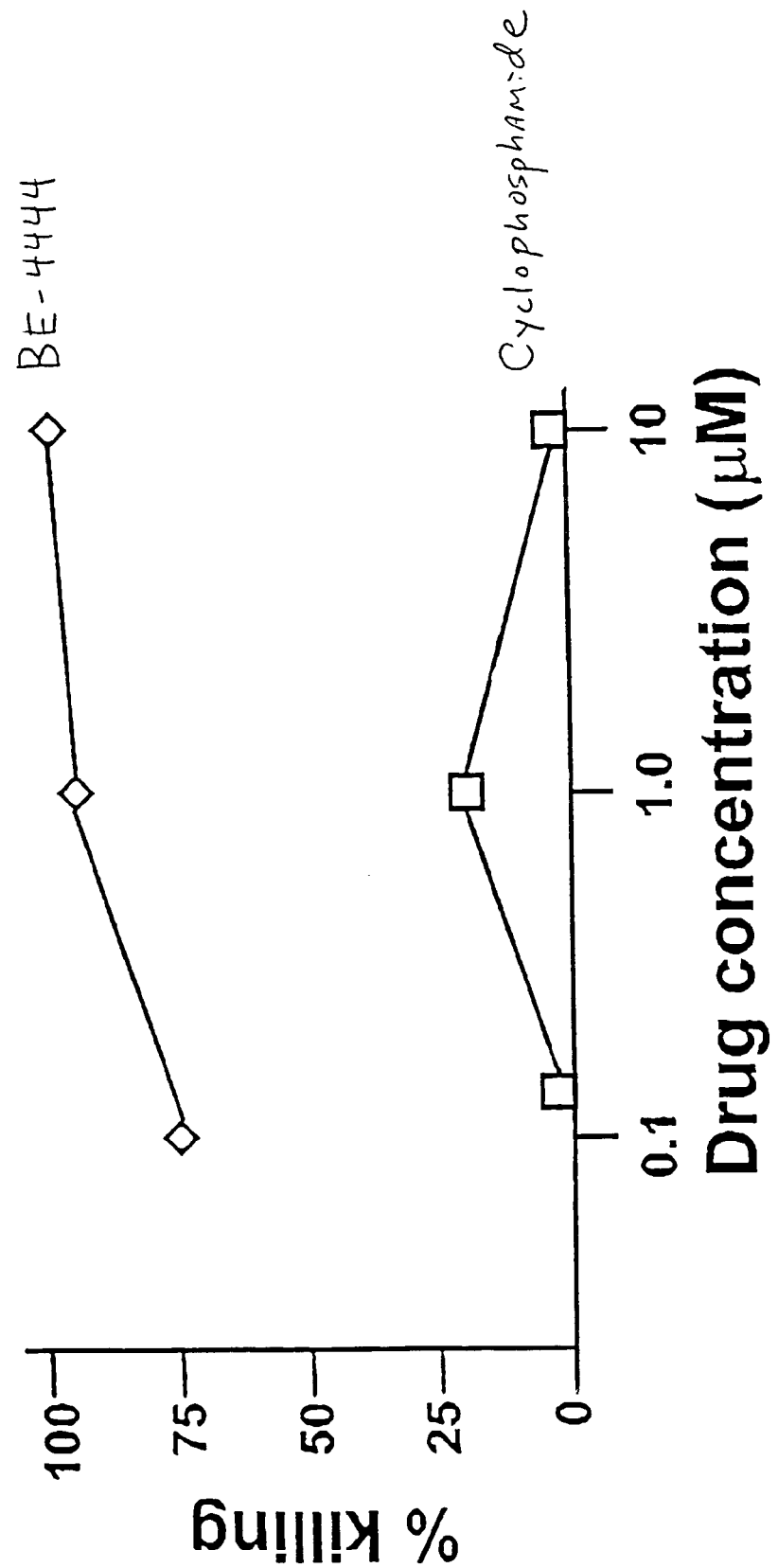
Figure 5:
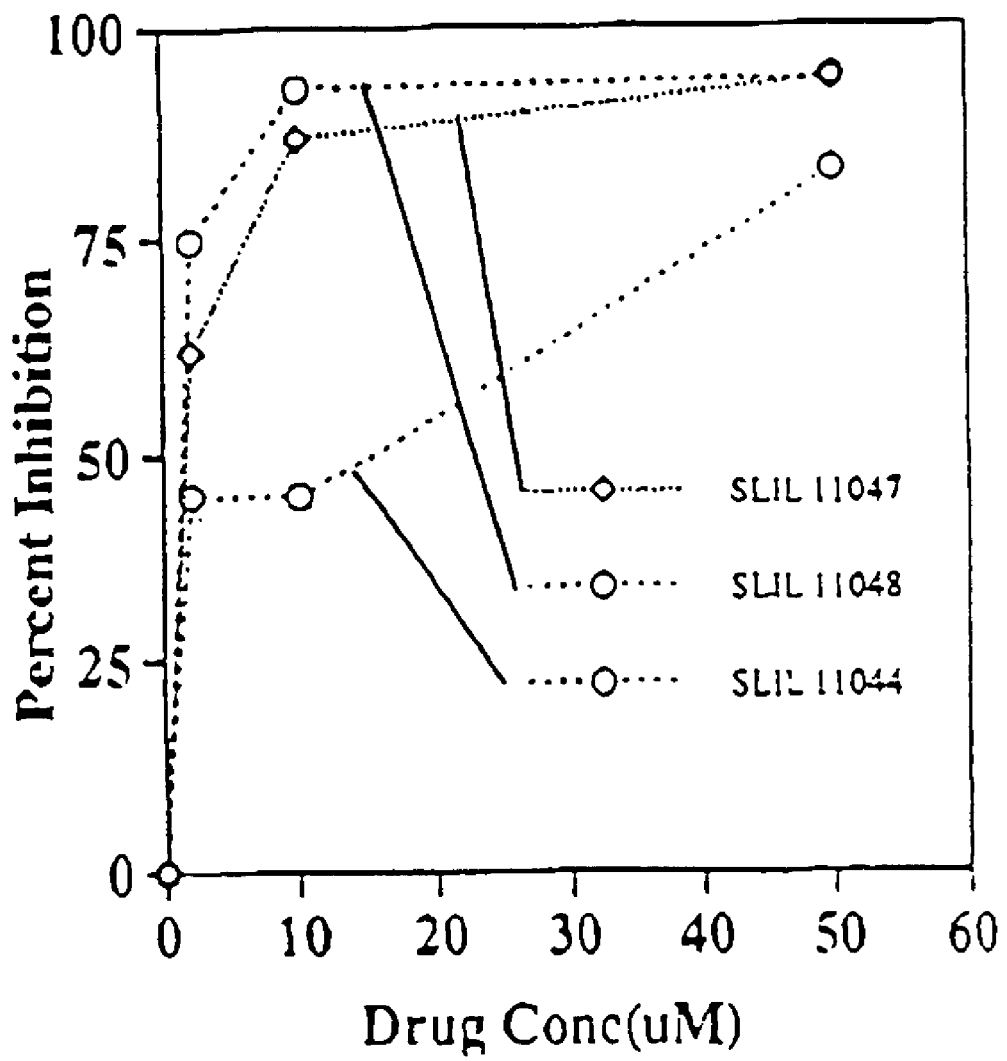
FIG. 5 is a graph depicting polyamine analog-mediated inhibition of PCNA$^+$ macrophage detection from peripheral HIV$^+$ sarcoid patients, using polyamine analogs SL-11047, SL-11048, and SL-11044.
Figure 6:
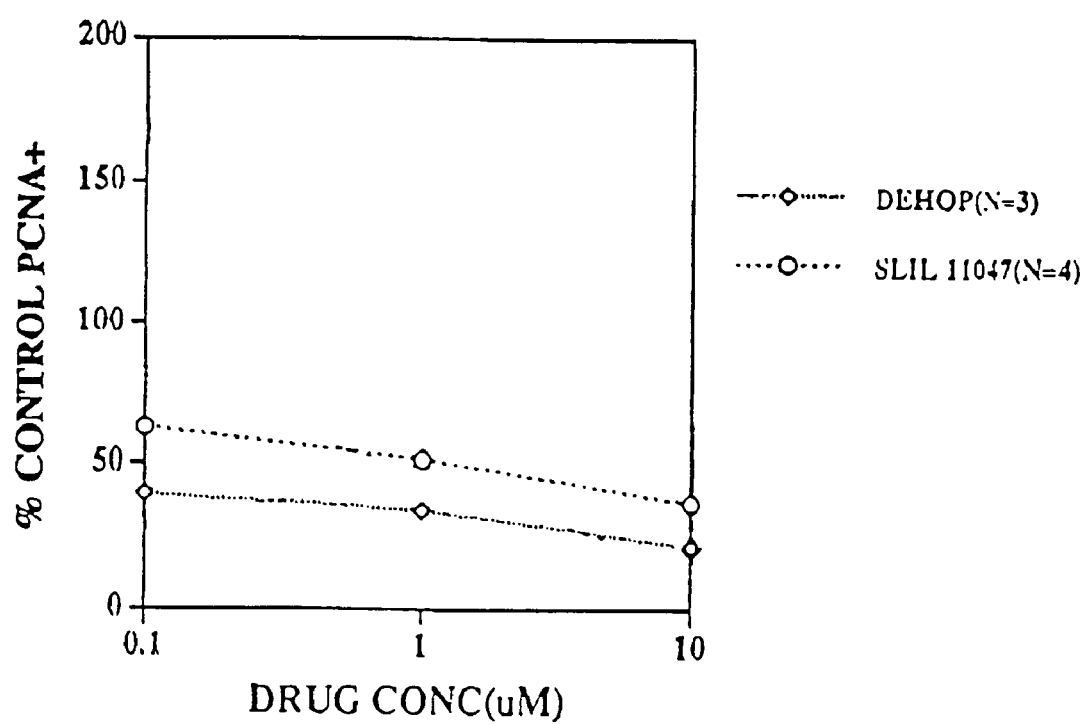
FIG. 6 is a graph depicting PCNA$^+$/CD14 cell survival after treatment with polyamine analogs DEHOP and SL-11047. N indicates the number of experiments performed.

A comparison of polyamine analogs SL-11037, SL-11038 (S'LIL Pharmaceuticals) and DENOP (SunPharm) on macrophage proliferation from the blood of one patient with AIDS dementia is shown in Table 2. All 3 agents showed inhibitory effects. FIG. 1B similarly shows that polyamine analog BE-4444 demonstrates potent killing of $PCNA^+$/$CD14^+$ cells. The data shown in FIG. 5 similarly demonstrate that polyamine analogs SL-11047, SL-11048 and SL-11044 (S'LIL Pharmaceuticals) are potent inhibitors of $PCNA^+$ macrophage detection from peripheral blood of $HIV^+$ sarcoid patient. 60% of input CD14 cells were $PCNA^+$; the assay was performed 96 hr after drug exposure and culture. The data shown in FIG. 6 demonstrate that polyamine analogs DEHOP and SL-11047 all decrease $PCNA^+$/CD14 cell survival. The data presented are averages of several (N) experiments performed. Thus, the data shown herein demonstrate that BE-4444, SL-11037, SL-11038, SL-11044, SL-11047, SL-11048, DEHOP and DENOP all demonstrated potent inhibition and/or killing of blood $PCNA^+$/$CD14^+$ cells.

TABLE 1

Effect of DEHOP and Cyclophosphamide (Cytoxan ®, Bristol-Myers Squibb) on $CD14^+$, $PCNA^+$ peripheral blood macrophage from an HIV dementia patient

| | #cells/10,000 PBMC | | |
|---|---|---|---|
| | $CD14^+$/$PCNA^+$ | $CD14^+$/$PCNA^-$ | total CD14 |
| DEHOP Concentration DEHOP | | | |
| 0 | 74 | 472 | 546 |
| 10 um | 31 | 89 | 120 |
| 2 | 28 | 182 | 210 |
| 0.4 | 25 | 222 | 247 |
| Cyclophosphamide Concentration Cyclophosphamide | | | |
| 0 | 74 | 472 | 546 |
| 5 µg/ml | 70 | 272 | 342 |
| 0.5 | 49 | 390 | 439 |
| 0.05 | 99 | 455 | 554 |
| 0.005 | 71 | 295 | 366 |

Patient CB at time 0:

% of $CD14^+$ that were $CD69^+$: 0

% of $CD14^+$ that were $PCNA^+$: 28% median SSC for all $CD14^+$: 420

TABLE 2

EFFECTS OF DRUGS SL-11037, SL-11038 AND DENOP ON CD14+, CD69+ AND CD14+, PCNA+ CELLS

*NO. OF CELLS/5,000

| | 0 DRUG | SL-11037 | | | SL-11038 | | | DENOP | | |
|---|---|---|---|---|---|---|---|---|---|---|
| | | 50 μM | 10 μM | 2 μM | 50 μM* | 10 μM | 2 μM | 50 μM | 10 μM* | 2 μM |
| CD14+, CD69+ | 35/5000 | 33/5000 | 49/5000 | 46/5000 | 26/5000 | 32/5000 | 30/5000 | 32/5000 | 23/5000 | 32/5000 |
| CD14+, PCNA+ | 64/5000 | 11/5000 | 32/5000 | 49/5000 | 24/5000 | 36/5000 | 104/5000 | 19/5000 | 23/5000 | 34/5000 |
| TOTAL CD14/PCNA | 388 | 79 | 116 | 276 | 104 | 205 | 356 | 43 | 50 | 149 |

TABLE 3

In-vitro inhibition of CD14+/PCNA antigen expression on peripheral a bloodmacrophage from HIV dementia patients

| | Concentration | % Inhibition | | | | |
|---|---|---|---|---|---|---|
| patient | DEHOP (um) | 50 | 10 | 2 | 0.4 | 0.08 |
| 1 | | 84 | 95 | 79 | | |
| 2 | | | 97 | 94 | 94 | |
| 3 | | | 58 | 62 | 66 | |
| 4 | | | | 75 | 25 | 19 |
| mean | | 84 | 83 +/− 22 | 78 +/− 13 | 62 +/− 34 | 19 |

Example 2

Suppression of In Vitro Cell Killing by Supernatants from Peripheral Blood from an AIDS Dementia Patient We have previously observed a cell killing effect of mononuclear cell supernatants from peripheral blood of patients with AIDS dementia. Pulliam et al. (1997) *Lancet* 349: 692-695. We tested a similarly prepared supernatant which was treated with the polyamine analog DEHOP.

Preparation of Mononuclear Cell Supernatants

To collect a maximum number of monocytes (both heavy and light), we used a one-step Percoll protocol. 1.5 mL whole heparinised blood was mixed with an equal volume of isotonic phosphate-buffered solution and layered over 5 mL Percoll at 1.087. The cells were centrifuged, washed, and resuspended in RPMI 1640 supplemented with 10% fetal calf serum at 10°/mL. To separate non-adherent lymphocytes from adherent monocytes, culture dishes were washed with RPMI after overnight incubation. The adherent cells were re-fed with RPMI and cultured for 7 days to obtain supernatants. Supernatants were clarified by centrifugation at 90,000 g over 25% sucrose overnight. The supernatant was filtered through a 0.22 μm syringe filter and stored at −70° C.

Brain Aggregate Cultures and Supernatant Treatment

Human fetal brain tissue from between 16 and 18 weeks' gestation was obtained from elective abortions for preparation of brain cell aggregates. These aggregates contain all the cells of the central nervous system including neurons, astrocytes, oligodendrocytes with accompanying myelin, and microglial cells. After 10 days in culture, and before experimentation, aggregates were tested for viability by trypan-blue exclusion. Aggregates were divided into flasks at 50 mg wet-weight in 2 mL exchange medium (DMEM with 15% fetal calf serum). Aggregates were treated with mononuclear cell supernatants (20%) for 3 days. The flasks contents were centrifuged; the supernatant was used for lactate dehydrogenase assay and the aggregate pellet for DNA fragmentation (programmed cell death) assay.

Quantification of Cell Death by ELISA

Lactate dehydrogenase is released on cell lysis. We used a cytotoxicity ELISA kit (Boehringer Mannheim). The brain aggregate supernatant was reacted with yellow tetrazolium salt and absorbance was read at 490 nm. The DNA fragmentation assay kit (Boehringer Mannheim) measures cytosolic oligonucleosome-bound DNA. The brain aggregate pellet was solubilised and used for this assay.

Electron Microscopy

Brain cell aggregates were treated with 20% supernatant from cultured CD14 cells from a demented AIDS patient. Treatment was for 72 h. After treatment, the aggregates were washed and fixed in Karnovsky's solution. The cells were post-fixed in 1% osmium tetroxide dehydrated for staining with uranyl acetate and lead citrate. Thin sections were examined in a JEOL 1OOSX electron microscope.

Figure 2:
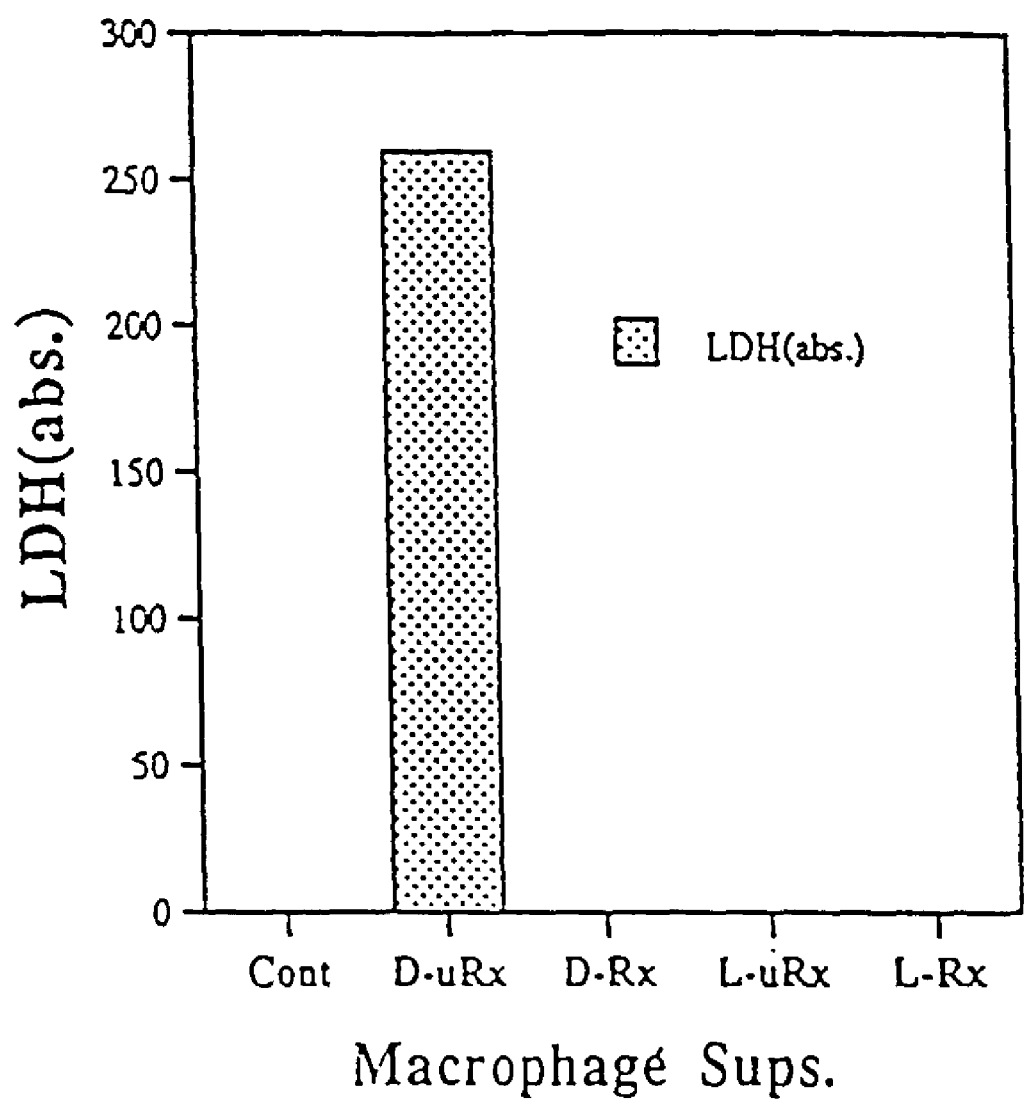
FIG. 2 is a bar graph denoting comparative in vitro cell toxicity of macrophage supernatants which have been treated (Rx) or not treated (uRx) with the polyamine analog DEHOP. Designations are as follows: Cont., control; D-uRx, AIDS dementia, no DEHOP; D-Rx, AIDS dementia, DEHOP; L-uRx, AIDS lymphoma, no DEHOP; L-Rx, lymphoma, DEHOP.

The results are shown in FIG. 2. Untreated macrophage supernatants from peripheral blood an AIDS dementia patient showed significant cell killing, which virtually disappeared if the preparations were treated with DEHOP. Non-dementia disease control did not show significant cell killing, either with or without DEHOP treatment.

Example 3

Detection of Proliferating Macrophages in Patients with Alzheimer's Disease Participants and Methods
Blood Samples Individuals with Alzheimer's disease dementia (6 patients) were recruited from Laguna Honda hospital, University of California at San Francisco, and San Francisco General hospital. Exclusion criteria included history of head injury, seizures, or multiple sclerosis, active opportunistic infection, active opportunistic central nervous system infection or lymphoma, cerebrovascular disease, major psychiatric illness, other known causes of dementia, or pre-existing causes of brain disorder. Participants or their representatives gave informed consent. Blood was obtained in accordance with the Committee on Human Research. Negative controls (6 patients) were recruited from laboratory personnel and gave informed consent. Non-AD diseased control categories were multiple sclerosis (2 patients), amyotrophic lateral sclerosis (2 patients), AIDS dementia (7 patients), and Parkinson's disease (2 patients).

Flow Cytometry for Monocyte Subsets 5 mL blood was obtained from patients and controls. 100 μL whole heparinised blood was stained with fluorescein-conjugated anti-CD14 (DAKO Corp.) and with phycoerythrin-conjugated anti-PCNA (Becton Dickinson). Red-blood cells were lysed by the addition of FACSLYSE solution (Becton Dickinson). The cell suspensions were centrifuged and the cell pellets resuspended in phosphate-buffered saline containing sodium azide and paraformaldehyde and stored at 4° C. To stain intracellularly for PCNA, cell pellets were resuspended in "Permeabilising Solution" (Becton Dickinson). Buffer was added to each tube, followed by centrifugation. Cell pellets were resuspended in buffer and stained with phycoerythrin-conjugated PCNA. The cells were washed, fixed, and stored as above.

Figure 4:
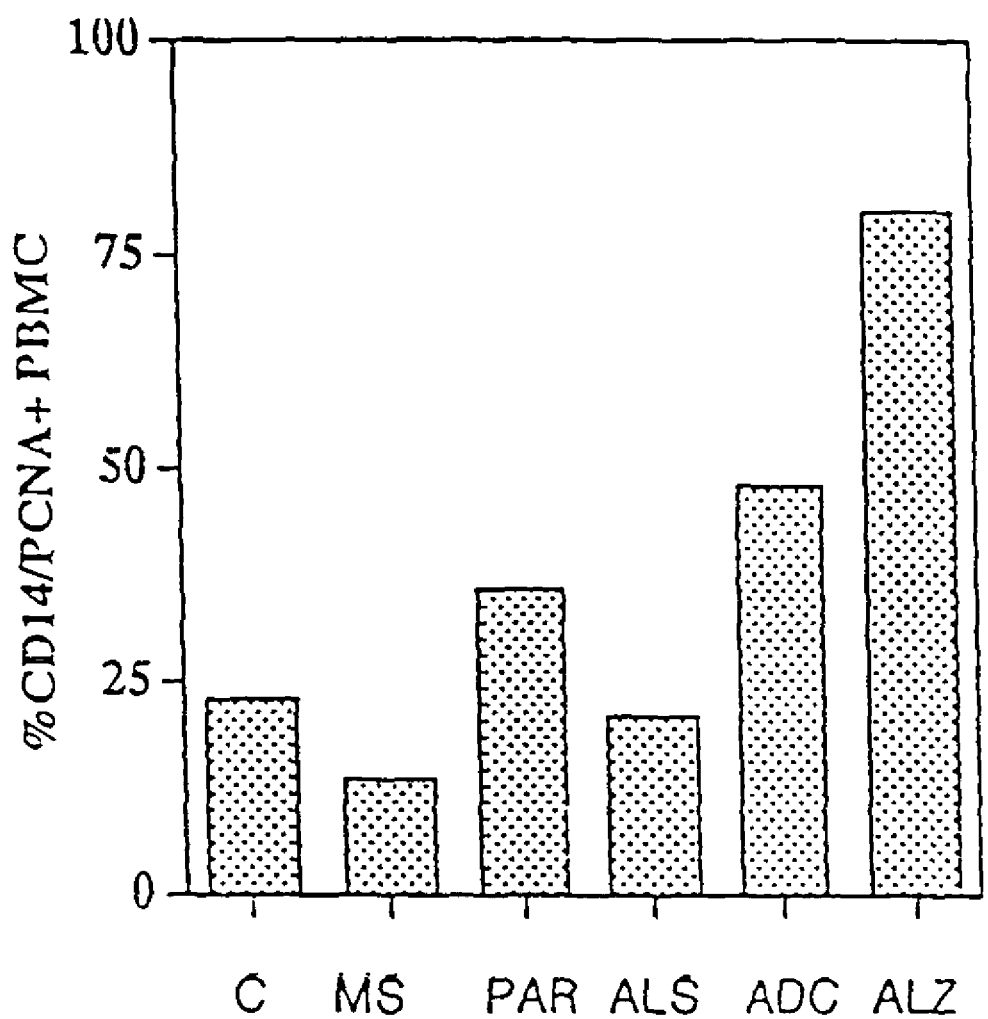
FIG. 4 is a bar graph depicting detection of proliferating macrophages (PCNA/CD14 cells) in the peripheral blood of patients with AD as compared to non-disease and disease controls. C: control (N=6); MS: multiple sclerosis (N=2); PAR: Parkinson's disease (N=2); ALS: Amyotrophic lateral sclerosis (N=2); ADC: AIDS dementia complex (N=7); ALZ: AD (N=6).

Cells were analysed with a FACSCAN flow cytometer (Becton Dickinson). At least 2000 cells per sample were analysed. Negative staining was defined as the area of dot plots that contained over 99% of isotype-stained (DAKO) "control cells". The results are shown in FIG. 4. The patients with AD displayed a significantly higher percentage of proliferating macrophages or non-disease controls as well as diseased controls, including AIDS dementia. Individual values (percentage PCNA/CD14 cells) were: (a) non-disease controls, 10; 16; 19; 20; 27; 46; (b) disease controls: ALS, 17; 25; Parkinson's, 27; 45; MS, 7; 20; HIV dementia, 6; 28; 37; 52; 54; 61; 96; (c) AD patients, 44; 47; 91; 97; 98; 100.

Thus, the data presented herein show that macrophage proliferation is characteristic of Alzheimer's disease.

Example 4

Effect of Polyamine Analogs on PCNA Expression of Peripheral Macrophages from Patients with AD Separation of Peripheral Blood Monocytes We had previously separated peripheral blood monocytes on Ficoll. We found that a standard Ficoll Hypaque separation gave lower yields of monocytes from demented patients than from HIV-infected controls (44 vs 67%, respectively). Several demented patients yielded under 10% of predicted, suggesting that a subset of monocytes was being missed. We then used Percoll gradient separation, which allows for denser cells to be captured. A two-step gradient was prepared in 15 mL conical tubes: bottom layer of 1.087 density Percoll, overlaid with 1.077 density. 1.5 mL whole heparinised blood was mixed with an equal volume of isotonic saline. This blood/saline was layered over the gradient and centrifuged. Cells from the 1.077 and 1.087 interfaces were collected combined, and washed in 5 volumes of RPMI 1640.

Figure 3:
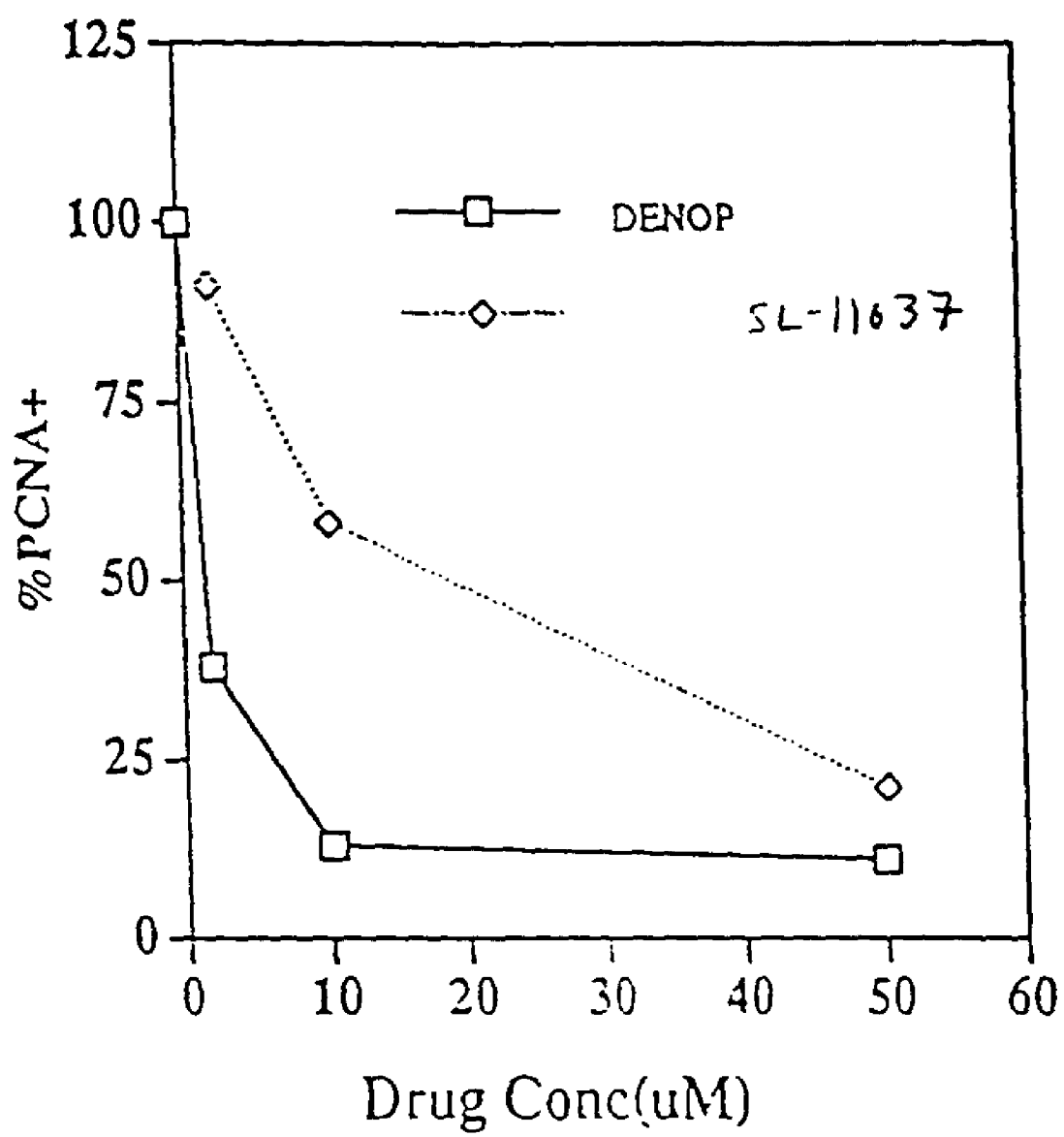
FIG. 3 is a graph depicting the effects of polyamine analogs DENOP and SL-11037 on macrophage proliferation, as evidenced by PCNA expression in CD14 cells. Macrophages were obtained from peripheral blood of patients with AD.

Five×$10^5$ PBMC's isolated through a 1.087 g/cc Percoll/saline gradient were exposed to varied concentrations of agent after baseline CD14/PCNA staining was performed as described in Example 3. The cells were cultured at 5×10 cells in RPM1-1640/10% fetal calf serum in a polypropylene tube (Falcon) at 37° C. for five days. After five days CD14/PCNA staining was performed on control and agent-treated cultures. FACSCAN analysis of PCNA-positive cells in control cultures was compared with agent-treated cultures and percentage of control PCNA/CD14 cells was calculated. Two polyamine analogs, DENOP (SunPharm; Florida) and SL-11037 were tested. As shown in FIG. 3, both agents significantly reduced the percentage of proliferating macrophages.

Example 5

Using Polyamine Analog to Treat an Individual with a Macrophage-Associated Dementia A 72-year-old male presents with increasing loss of memory and confusion. A blood sample is obtained, and the percentage of PCNA-expressing CD14 cells is significantly elevated over the control. The patient is given DESPM (a polyamine analog) at 125 mg/m$^2$/day for six days, repeated every three weeks. Blood samples are obtained routinely to monitor the level of PCNA-expressing CD14 cells.

Example 6

Effects of Polyamine Analog Diethylhomospermine (DEHOP) on Chemotherapy Resistant AIDS Related Lymphoma Patients Four patients who had failed standard chemotherapy for treatment of their AIDS related lymphoma (therapy included at least CHOP chemotherapy up to six cycles) were evaluated for response to DEHOP administration in vivo. Patients had blood drawn pre administration of drug for evaluation of macrophage activation. This blood was also evaluated for response to DEHOP in vitro. The trial was set up to evaluate clinical response to drug given for 5 days subcutaneously (sq) at a dose of 25 mg/m$^2$ (2 patients) and 50 mg/m$^2$ (2 patients). Blood was obtained at 1 week after completion of the first and second cycles of therapy. The blood specimens were evaluated for macrophage proliferation (proliferating cell nuclear antigen, PCNA expression), and activation (percentage CD69 expression). Response to therapy was evaluated by direct observation of tumor (3 patients) and persistence or resolution of symptoms (1 patient with GI lymphoma).

Figure 7:
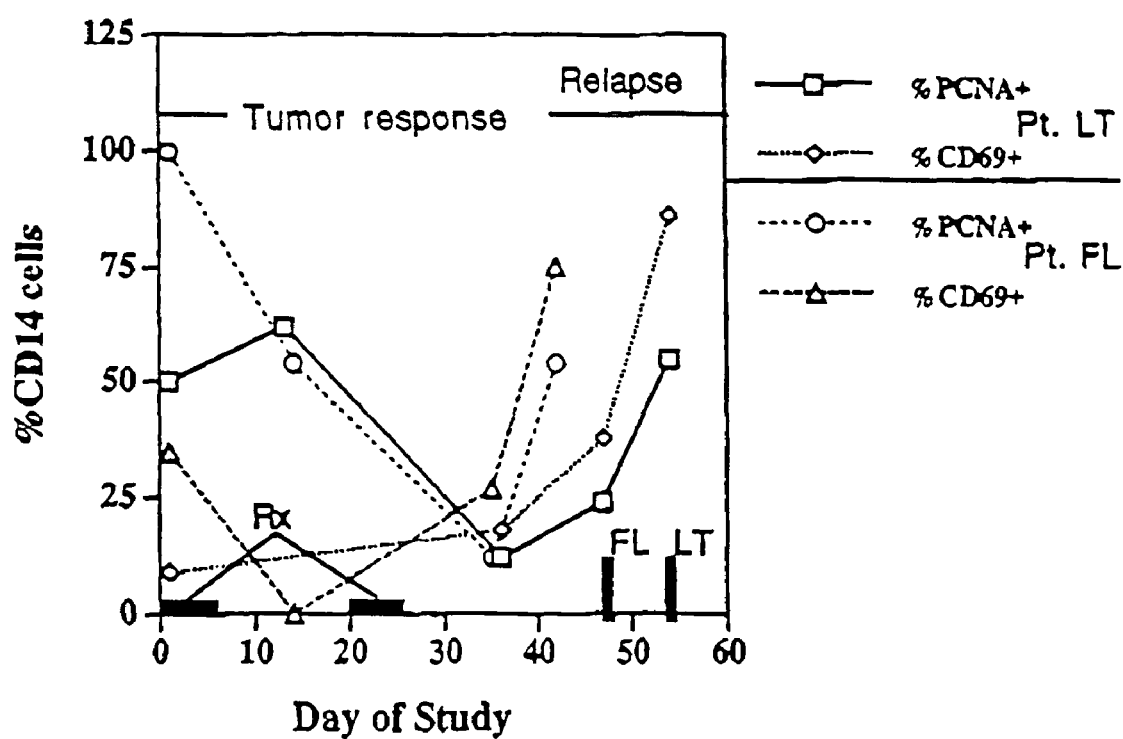
FIG. 7 is a graph showing the in vivo responses to DEHOP of CD14$^+$ cells in a peripheral blood mononuclear cell preparation (PBMC) from the 2 AIDS lymphoma patients, FL and LT.

To test whether patient macrophages would respond to administration of DEHOP in vitro, CD14 cells in a peripheral blood mononuclear cell preparation (PBMC) were exposed to different concentrations of DEHOP and the proportion of CD14 positive cells surviving at the end of 5 days of culture was assessed in drug treated cells as compared to controls. Specimens obtained pre chemotherapy were compared to specimens obtained 2 weeks post therapy. Table 4 summarizes CD14$^+$ cell responses to DEHOP in vitro in the 4 AIDS lymphoma patients evaluated; FIG. 7 shows the CD14$^+$ cell response to DEHOP in vivo. For patient FL, the first specimen was obtained one day after the first cycle of DEHOP; the second specimen was obtained one week later. The effective dose 50 (where 50% of cells were killed), and effective dose 80 (where 80% of cells were killed) were calculated for each set of patient specimens exposed to DEHOP in vitro. In post in vivo DEHOP administration blood specimens, patient FTJ was persistently resistant to drug whereas patient LT and FL, both of whom responded clinically to DEHOP, showed marked drug sensitivity in vitro.

To determine whether kinetics of macrophage activation parameters predicted response to DEHOP therapy, CD14 cell analysis results from the 2 patients who had demonstrated a clinical response were combined and plotted in FIG. 7. FIG. 7 shows that both patients showed elevated levels of PCNA/CD69 expression at initiation of therapy, a decrease during tumor response and an increase just prior to tumor relapse. These values generally decreased after administration of drug (shown in the dark shaded box along the x-axis) and a low to background level of expression of all parameters was observed for both patients on day 35 after initiation of study. Both patients had objective and subjective responses to DEHOP at this time. Because of intercurrent medical problems the patients were not allowed to receive a third cycle of DEHOP and both patients ultimately relapsed, FL on day 47 and LT on day 54. All of the macrophage activation parameters increased in both patients prior to their clinical objective tumor relapse.

In contrast to the 2 patients who responded to DEHOP clinically, where macrophage activation parameters seemed to predict sensitivity and response to drug, patient FTJ and WA showed no change in PCNA expression or CD69 expression after the first cycle of DEHOP and had no tumor response to drug.

The information obtained by evaluating drug sensitivity of patient macrophages in vitro to DEHOP exposure and tumor response to DEHOP in vivo suggests that response of the macrophages to DEHOP either correlated or showed some association with tumor sensitivity to DEHOP treatment in vivo. These data suggest that sensitivity to the polyamine analog DEHOP predicts tumor response to the drug and that at time of relapse the re-expression of activated/proliferating macrophages correlates with that tumor response. One interpretation of this data is that if patients have circulating macrophages that are activated/proliferating that respond to DEHOP, those patients may be candidates for a response to the drug in vivo.

TABLE 4

CD14 Cell Polyamine Analog Sensitivity: In vitro dose response in NHL patient PBMC; total $CD14^+$ cell survival, $ED_{50}$ and $ED_{80}$

| Patient | Specimen | $ED_{50 \mu M}$ | $ED_{80 \mu M}$ | Response to Therapy |
| --- | --- | --- | --- | --- |
| FTJ | Pre | 1.0 | >10 | None |
|  | Post | >10 | >10 |  |
| WWA | Pre | 10 | >10 | None |
| LT | Pre | 10 | >10 | Clinical Response |
|  | Post | 0.1 | 0.8 |  |
| FL | Pre | <0.1 | 1.0 | >50% objective measured tumor |
|  | Post | <0.1 | 0.1 | response after first week of Rx |

Although the foregoing invention has been described in some detail by way of illustration and example for purposes of clarity of understanding it will be apparent to those skilled in the art that certain changes and modifications will be practiced. Therefore, the description and examples should not be construed as limiting the scope of the invention, which is delineated by the appended claims.

What is claimed is:

1. A method of treating a subject afflicted with, or at risk for, HIV-associated dementia or delaying development or onset of HIV-associated dementia in said subject comprising administering to said subject effective amount of a composition comprising mitoguazone or a salt of mitoguazone, wherein the patient does not have AIDS-related non-Hodgkin's lymphoma.

2. The method of claim 1, wherein the composition comprises mitoguazone dihydrochloride.

3. A method of modulating macrophage proliferation in an individual afflicted with, or at risk for, HIV-associated dementia comprising administering to the individual an effective amount of a composition comprising mitoguazone or a salt of mitoguazone, wherein the patient does not have AIDS-related non-Hodgkin's lymphoma.

4. The method of claim 3, wherein the composition comprises mitoguazone dihydrochloride.

5. A method of modulating macrophage proliferation in an individual afflicted with, or at risk for, a macrophage-associated disease comprising administering to the individual an effective amount of a composition comprising mitoguazone or a salt of mitoguazone, wherein the disease is HIV-associated dementia or non-HIV-associated dementia, wherein the patient does not have AIDS-related non-Hodgkin's lymphoma.

6. The method of claim 5, wherein the composition comprises mitoguazone dihydrochloride.

7. A method of treating a subject afflicted with, or at risk for, a macrophage-associated disease or delaying onset or development of a macrophage-associated disease in said subject comprising administering to said subject an effective amount of a composition comprising mitoguazone or a salt of mitoguazone to reduce macrophage proliferation in said subject, wherein the disease is HIV-associated dementia or non-HIV-associated dementia, wherein the patient does not have AIDS-related non-Hodgkin's lymphoma.

8. The method of claim 7, wherein the composition comprises mitoguazone dihydrochloride.

* * * * *

UNITED STATES PATENT AND TRADEMARK OFFICE
CERTIFICATE OF CORRECTION

| | | |
|---|---|---|
| PATENT NO. | : 8,008,353 B2 | Page 1 of 1 |
| APPLICATION NO. | : 11/022153 | |
| DATED | : August 30, 2011 | |
| INVENTOR(S) | : McGrath | |

It is certified that error appears in the above-identified patent and that said Letters Patent is hereby corrected as shown below:

In claim 1, column 26, line 7, please insert --an-- so that it reads --to said subject an effective amount--.

Signed and Sealed this
Sixth Day of March, 2012

David J. Kappos
*Director of the United States Patent and Trademark Office*